(12) United States Patent
Tobelmann et al.

(10) Patent No.: US 7,076,438 B1
(45) Date of Patent: Jul. 11, 2006

(54) SYSTEMS AND METHODS FOR DETERMINING NUTRIENTS WITHIN DIETARY INTAKE

(75) Inventors: Rosemary Tobelmann, Plymouth, MN (US); Michael T. Goebel, Plymouth, MN (US); Ann Marie Albertson, Deephaven, MN (US)

(73) Assignee: General Mills, Inc., Minneapolis, MN (US)

( * ) Notice: Subject to any disclaimer, the term of this patent is extended or adjusted under 35 U.S.C. 154(b) by 428 days.

(21) Appl. No.: 09/951,775

(22) Filed: Sep. 14, 2001

(51) Int. Cl.
*G06F 17/60* (2006.01)
*G06F 17/00* (2006.01)
*G06F 3/00* (2006.01)

(52) U.S. Cl. .............................. 705/7; 705/1; 128/921; 708/132

(58) Field of Classification Search .................. 705/1, 705/2, 3, 7, 10, 28, 29, 500; 600/300; 128/921; 177/25.16; 434/127; 708/130, 131, 133, 708/105; 702/173
See application file for complete search history.

(56) References Cited

U.S. PATENT DOCUMENTS

| | | | | |
|---|---|---|---|---|
| 5,233,520 A * | 8/1993 | Kretsch et al. | ............. | 600/300 |
| 5,411,757 A * | 5/1995 | Buist et al. | ................. | 426/656 |
| 5,412,564 A * | 5/1995 | Ecer | .......................... | 600/300 |
| 5,691,927 A * | 11/1997 | Gump | ........................ | 708/131 |
| 5,704,350 A * | 1/1998 | Williams, III | ............... | 600/300 |
| 5,836,312 A * | 11/1998 | Moore | ........................ | 128/921 |
| 5,890,128 A * | 3/1999 | Diaz et al. | ...................... | 705/2 |
| 6,061,734 A * | 5/2000 | London | ....................... | 709/238 |
| 6,083,006 A * | 7/2000 | Coffman | ..................... | 129/921 |
| 6,131,812 A * | 10/2000 | Schneider | .................... | 235/385 |
| 6,179,778 B1 * | 1/2001 | Leonov et al. | .............. | 600/300 |
| 6,283,914 B1 * | 9/2001 | Mansfield et al. | .......... | 600/300 |
| 6,464,992 B1 * | 10/2002 | Jacobson et al. | ........... | 424/401 |
| 6,527,712 B1 * | 3/2003 | Brown et al. | ................ | 600/300 |
| 6,652,455 B1 * | 11/2003 | Kocher | ........................ | 600/300 |

FOREIGN PATENT DOCUMENTS

WO    WO88/01770    3/1988

OTHER PUBLICATIONS

Dietetics System Technical Manual, 1995.*

(Continued)

*Primary Examiner*—John W. Hayes
*Assistant Examiner*—Igor N. Borissov
(74) *Attorney, Agent, or Firm*—John A. O'Toole; Douglas J. Taylor

(57) ABSTRACT

The present invention uses market research data to access nutrient intakes of a population. Dietary collection using 24-hour recall generally does not reflect a pattern of "usual" intake behavior for a population group. To determine the impact of food consumption patterns on nutrient intake, a unique methodology using 14-day food diary was developed. The food industry has traditionally used detailed food records to track the consumption of specific branded food items and monitor the growth of food categories, but some of the most valuable databases available concerning longer-term (e.g., 14-day) food intake do not record portion size on an individual consumption basis. Other databases based on shorter-term (24-hour recall) survey periods record portion sizes but are not very representative of eating habits. The preferred exemplary embodiment integrates two such databases with a third data set providing detailed nutrient information for each of a wide variety of foods consumed to provide a combined database for processing nutrient intake reports using statistical analysis. This flexible system allows the user to categorize the population based on "usual" consumption of food categories, specific foods and/or specific brands of foods and determine dietary differences versus their "non-using" counterparts.

26 Claims, 19 Drawing Sheets

Example Dietary Intake Study System

OTHER PUBLICATIONS

DeMaio et al. Research on the Continuing Survey of Food Intakes by Individuals. Processings of the Selection on Survey Research Methods, Alexandria, VA: American Statistical Association pp. 1021-1026, 1993.*

USDA Continuing Survey of Food Intakes by Individuals; the Internet print out.*

Paeratakul et al. "Americans on diet: Results from the 1994-1996 Continuing Survey of Food Intakes by Individuals", Journal of The American Dietetic Association.*

"Net Viewer User's Manual", the NPD Group National Eating Trends Service (Feb. 2000).

NDP Sample Diary.

NPD Foods and Beverages Examined by Net, Category Structure Mar. '97-Feb. '98.

"What's On the CSFII 1994-96, 1998 CD-ROM," U.S. Dept. of Agriculture, Agricultural Research Service (Jun. 2000).

Albertson, A.M. et al. "The Use Of Market Research Data To Access Nutrient Intake Of The American Population," the Fourth International Conference on Dietary Assessment Methods, Tucson, AZ (Sep. 17-20, 2000).

Abstracts from the Fourth International Conference on Dietary Assessment Methods, Tucson, AZ (Sep. 17-20, 2000).

National Eating Trends®, 1 page.

Letter re: National Eating Trends Diary—Changes to Special Label Codes (Feb. 17, 1999).

Letter re NET, SnackTrack and Pantry Audit services (Nov. 19, 1998).

* cited by examiner

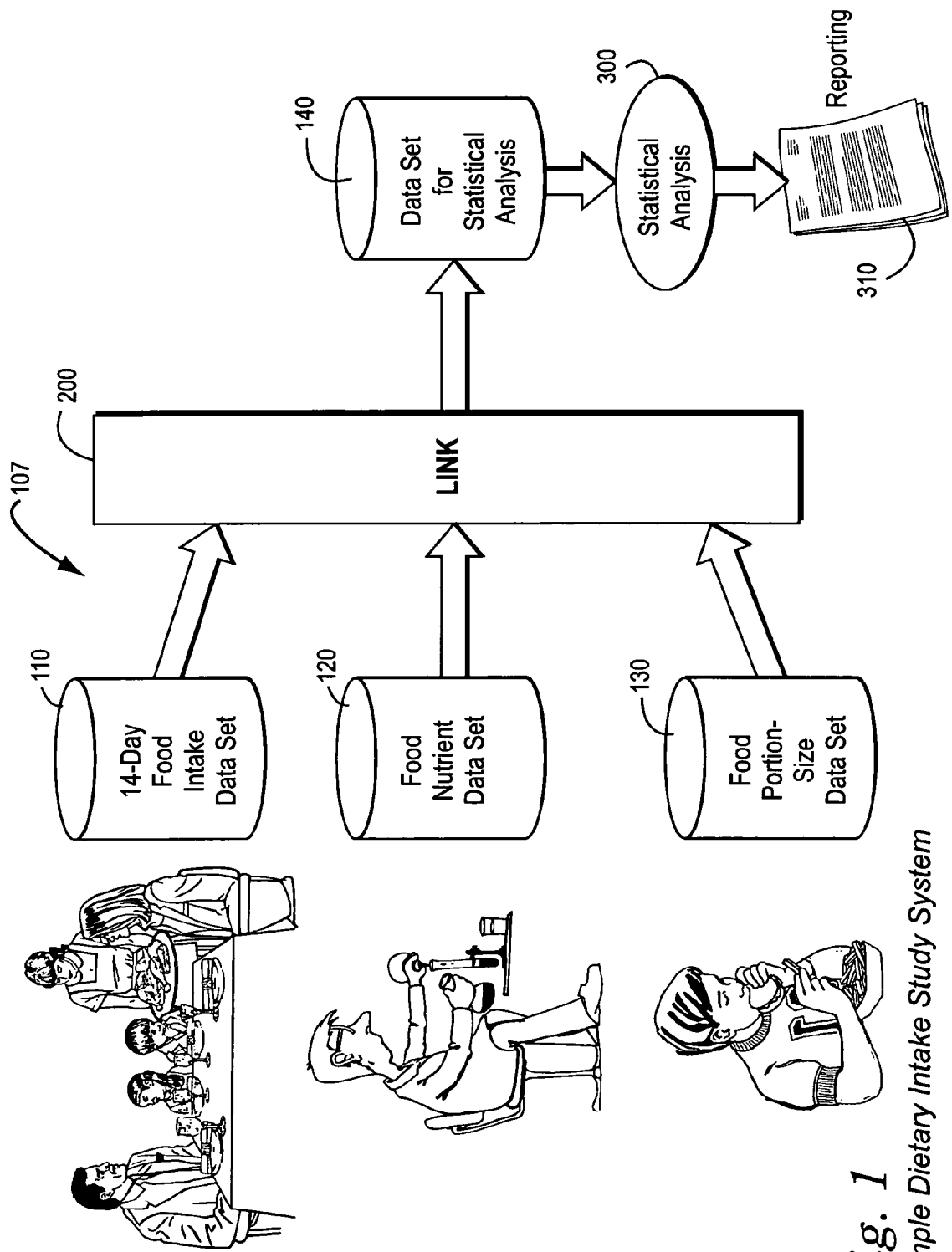
Fig. 1  Example Dietary Intake Study System

Example Data Set Merge

*Example Data Set Linkage*

*Example Overall Process*

Example Computation System

Example Computation System Implementation

Example Software Architecture

Example More Detailed Data Set Linkage

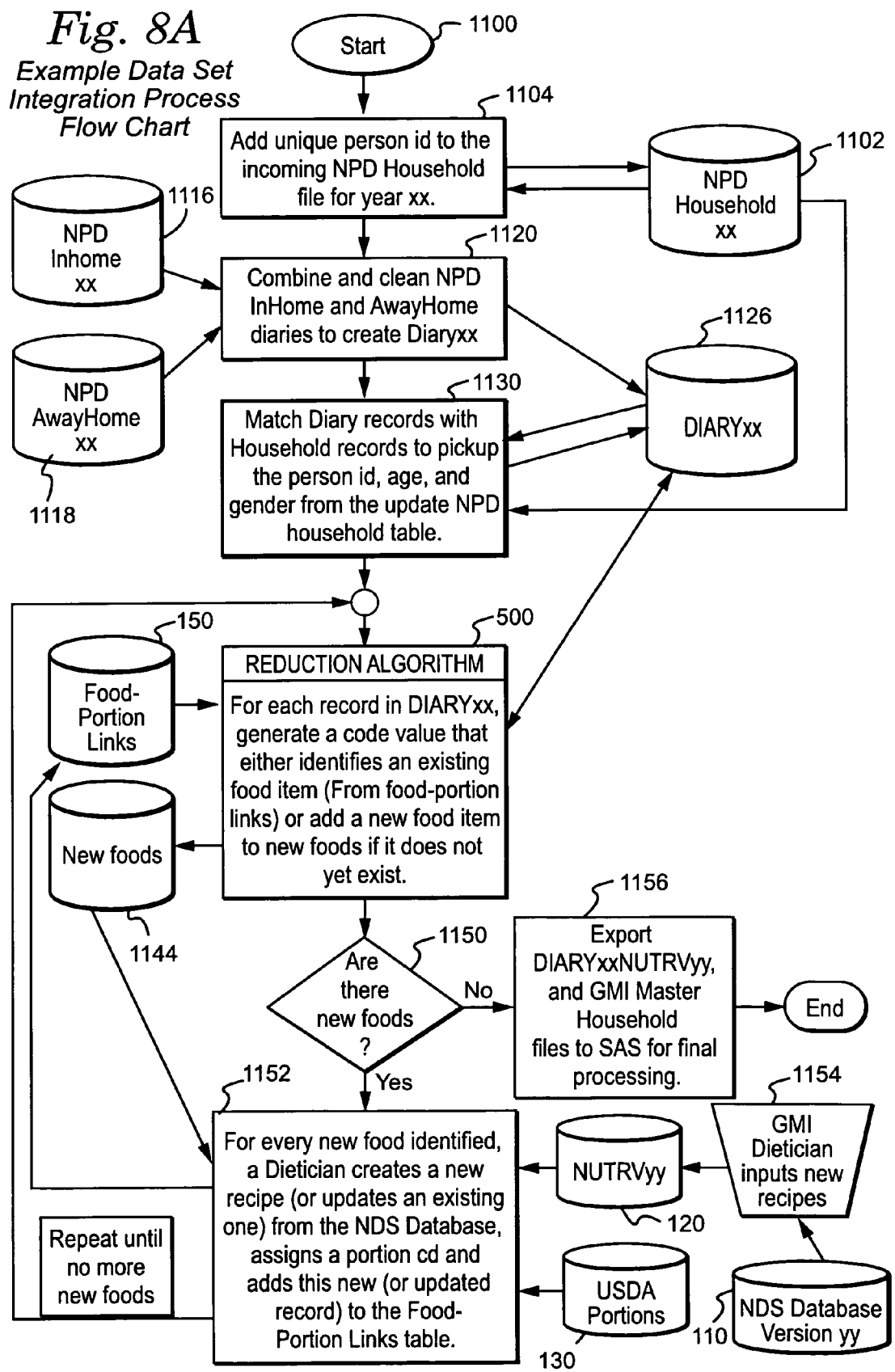

| Person | FOOD_CD | Day | Meal | CAT_CD | TY_CD | FRM_CD | CHAR_CD | FLVR_CD | CLS_CD | PREP_MTHD_CD | PKG_TY_CD | SPC_LBL_CD | Portion_CD |
|---|---|---|---|---|---|---|---|---|---|---|---|---|---|
| 108538 | 2 | 2 | 27 | 1 | | 12 | | | 077 | 02 | | 0 | 00 |
| 108538 | 2 | 2 | 44 | 1 | | | 3 | | | 10 | | | 02 |
| 108538 | 2 | 2 | 52 | 1 | | | 0 | | 048 | 01 | | | 00 |

| Person | FOOD_CD | Day | Meal | CAT_CD | TY_CD | FRM_CD | CHAR_CD | FLVR_CD | CLS_CD | PREP_MTHD_CD | PKG_TY_CD | SPC_LBL_CD | Portion_CD |
|---|---|---|---|---|---|---|---|---|---|---|---|---|---|
| 108538 | 2 | 2 | 27 | 1 | | 12 | | | 077 | 02 | | 0 | 00 |
| 108538 | 2 | 2 | 44 | 1 | | | 3 | | | 10 | | | 02 |
| 108538 | 2 | 2 | 52 | 1 | | | 0 | | 048 | 01 | | | 00 |

| Person | FOOD_CD | Day | Meal | CAT_CD | TY_CD | FRM_CD | CHAR_CD | FLVR_CD | CLS_CD | PREP_MTHD_CD | PKG_TY_CD | SPC_LBL_CD | Portion_CD |
|---|---|---|---|---|---|---|---|---|---|---|---|---|---|
| 108538 | 271154 | 2 | 2 | 27 | 1 | 12 |   | 077 | 02 |   | 00 |   | 6004 |
| 108538 |   | 2 | 2 | 44 | 1 |   | 3 |   | 10 |   | 02 | 0 |   |
| 108538 |   | 2 | 2 | 52 | 1 |   | 0 | 048 | 01 |   | 00 |   |   |

| Person | FOOD_CD | Day | Meal | CAT_CD | TY_CD | FRM_CD | CHAR_CD | FLVR_CD | CLS_CD | PREP_MTHD_CD | PKG_TY_CD | SPC_LBL_CD | Portion_CD |
|---|---|---|---|---|---|---|---|---|---|---|---|---|---|
| 108538 | 271154 | 2 | 2 | 27 | 1 | 12 |   | 077 | 02 |   | 00 |   | 6004 |
| 108538 | 441882 | 2 | 2 | 44 | 1 |   | 3 |   | 10 |   | 02 | 0 | 4100 |
| 108538 | 5213731 | 2 | 2 | 52 | 1 |   | 0 | 048 | 01 |   | 00 |   | 5478 |

| COMBO_KEY | CAT_CD | CMBNTN_COL | COL_NM | CMBNTN_VAL |
|---|---|---|---|---|
| 1017 | 27 | TYPE | TY_CD | 0,1,8 |
| 1018 | 27 | TYPE | TY_CD | 2,7 |
| 1019 | 27 | FORM | FRM_CD | 02 |
| 1020 | 27 | FORM | FRM_CD | 00,09,11,12,13,90,95 |
| 1021 | 27 | FLAVOR | FLVR_CD | 010-012,036 |
| 1022 | 27 | FLAVOR | FLVR_CD | 013-014,037,046-055 |
| 1023 | 27 | FLAVOR | FLVR_CD | 015-024,035,038-045,056-065,362-445,623-629 |
| 1024 | 27 | FLAVOR | FLVR_CD | 025-026 |
| 1025 | 27 | FLAVOR | FLVR_CD | 066-075 |
| 1026 | 27 | FLAVOR | FLVR_CD | 076 |
| 1027 | 27 | FLAVOR | FLVR_CD | 000,001,077,095,111,170-316,318-361 |
| 1028 | 27 | FLAVOR | FLVR_CD | 078,110,112 |
| 1029 | 27 | FLAVOR | FLVR_CD | 079-080,114 |
| 1030 | 27 | FLAVOR | FLVR_CD | 081,616-618 |
| 1031 | 27 | FLAVOR | FLVR_CD | 082 |
| 1032 | 27 | FLAVOR | FLVR_CD | 083,446-450 |
| 1033 | 27 | FLAVOR | FLVR_CD | 084 |
| 1034 | 27 | FLAVOR | FLVR_CD | 085 |
| 1035 | 27 | FLAVOR | FLVR_CD | 086 |
| 1036 | 27 | FLAVOR | FLVR_CD | 087,634,635 |
| 1037 | 27 | FLAVOR | FLVR_CD | 100-108,125,611-614,630-633 |
| 1038 | 27 | FLAVOR | FLVR_CD | 113,115,136,139,615 |
| 1039 | 27 | FLAVOR | FLVR_CD | 128 |
| 1040 | 27 | FLAVOR | FLVR_CD | 130,129,131,132 |
| 1041 | 27 | FLAVOR | FLVR_CD | 133,127,135,137 |
| 1042 | 27 | FLAVOR | FLVR_CD | 134,126,138,140,451-609,636-638 |
| 1043 | 27 | FLAVOR | FLVR_CD | 141 |
| 1044 | 27 | FLAVOR | FLVR_CD | 142 |
| 1045 | 27 | FLAVOR | FLVR_CD | 145 |
| 1046 | 27 | FLAVOR | FLVR_CD | 146 |
| 1047 | 27 | FLAVOR | FLVR_CD | 147-150,155-165 |
| 1048 | 27 | FLAVOR | FLVR_CD | 099,151 |
| 1049 | 27 | FLAVOR | FLVR_CD | 088,154,620-622 |
| 1050 | 27 | FLAVOR | FLVR_CD | 610 |
| 1051 | 27 | FLAVOR | FLVR_CD | 619 |
| 1052 | 27 | FLAVOR | FLVR_CD | 317 |
| 1053 | 27 | PACKAGE TYPE | PKG_TY_CD | 01,02 |
| 1054 | 27 | PACKAGE TYPE | PKG_TY_CD | 00,03,04,05,06,07,08,09,10 |
| 1055 | 27 | SPECIAL LABEL CODE | SPC_LBL_CD | 00,02,03,04,05,06,07,10,11,12,23-28,32 |
| 1056 | 27 | SPECIAL LABEL CODE | SPC_LBL_CD | 01,08,09,21,22,29,30,31 |
| 3017 | 27 | SPECIAL LABEL CODE | SPC_LBL_CD | 33 |
| 3123 | 27 | SPECIAL LABEL CODE | SPC_LBL_CD | 34 |
| 3287 | 27 | FLAVOR | FLVR_CD | 004 |

| Person | FOOD_CD | Day | Meal | CAT_CD | TY_CD | FRM_CD | CHAR_CD | FLVR_CD | CLS_CD | PREP_MTHD_CD | PKG_TY_CD | SPC_LBL_CD | Portion_CD |
|---|---|---|---|---|---|---|---|---|---|---|---|---|---|
| 108538 | 2 | 2 | 27 | 1 | 12 | | 077 | | 02 | | 0 | | 00 |

*Fig. 9F*

| COMBO_KEY | CAT_CD | CMBNTN_COL | COL_NM | CMBNTN_VAL |
|---|---|---|---|---|
| 1017 | 27 | TYPE | TY_CD | 0,1,8 |

*Fig. 9G*

| COMBO_KEY | CAT_CD | CMBNTN_COL | COL_NM | CMBNTN_VAL |
|---|---|---|---|---|
| 1020 | 27 | FORM | FORM_CD | 00,09,11,12,13,90,95 |

*Fig. 9H*

| COMBO_KEY | CAT_CD | CMBNTN_COL | COL_NM | CMBNTN_VAL |
|---|---|---|---|---|
| 1027 | 27 | FLAVOR | FLVR_CD | 000,001,077,095,111,170-318,318-361 |

*Fig. 9I*

| COMBO_KEY | CAT_CD | CMBNTN_COL | COL_NM | CMBNTN_VAL |
|---|---|---|---|---|
| 1054 | 27 | PACKAGE TYPE | PKG_TY_CD | 00,03,04,05,06,07,08,09,10 |

*Fig. 9J*

| COMBO_KEY | CAT_CD | CMBNTN_COL | COL_NM | CMBNTN_VAL |
|---|---|---|---|---|
| 1055 | 27 | SPECIAL LABEL CODE | SPC_LBL_CD | 00,02,03,04,05,06,07,10,23-28,32 |

*Fig. 9K*

| COMBO_KEY | CAT_CD | CMBNTN_COL | COL_NM | CMBNTN_VAL |
|---|---|---|---|---|
| 1017 | 27 | TYPE | TY_CD | 0,1,8 |
| 1018 | 27 | TYPE | TY_CD | 2,7 |
| 1019 | 27 | FORM | FRM_CD | 02 |
| 1020 | 27 | FORM | FRM_CD | 00,09,11,12,13,90,95 |
| 1021 | 27 | FLAVOR | FLVR_CD | 010-012,036 |
| 1022 | 27 | FLAVOR | FLVR_CD | 013-014,037,046-055 |
| 1023 | 27 | FLAVOR | FLVR_CD | 015-024,035,038-045,056-065,362-445,623-629 |
| 1024 | 27 | FLAVOR | FLVR_CD | 025-026 |
| 1025 | 27 | FLAVOR | FLVR_CD | 066-075 |
| 1026 | 27 | FLAVOR | FLVR_CD | 076 |
| 1027 | 27 | FLAVOR | FLVR_CD | 000,001,077,095,111,170-316,318-361 |
| 1028 | 27 | FLAVOR | FLVR_CD | 078,110,112 |
| 1029 | 27 | FLAVOR | FLVR_CD | 079-080,114 |
| 1030 | 27 | FLAVOR | FLVR_CD | 081,616-618 |
| 1031 | 27 | FLAVOR | FLVR_CD | 082 |
| 1032 | 27 | FLAVOR | FLVR_CD | 083,446-450 |
| 1033 | 27 | FLAVOR | FLVR_CD | 084 |
| 1034 | 27 | FLAVOR | FLVR_CD | 085 |
| 1035 | 27 | FLAVOR | FLVR_CD | 086 |
| 1036 | 27 | FLAVOR | FLVR_CD | 087,634,635 |
| 1037 | 27 | FLAVOR | FLVR_CD | 100-108,125,611-614,630-633 |
| 1038 | 27 | FLAVOR | FLVR_CD | 113,115,136,139,615 |
| 1039 | 27 | FLAVOR | FLVR_CD | 128 |
| 1040 | 27 | FLAVOR | FLVR_CD | 130,129,131,132 |
| 1041 | 27 | FLAVOR | FLVR_CD | 133,127,135,137 |
| 1042 | 27 | FLAVOR | FLVR_CD | 134,126,138,140,451-609,636-638 |
| 1043 | 27 | FLAVOR | FLVR_CD | 141 |
| 1044 | 27 | FLAVOR | FLVR_CD | 142 |
| 1045 | 27 | FLAVOR | FLVR_CD | 145 |
| 1046 | 27 | FLAVOR | FLVR_CD | 146 |
| 1047 | 27 | FLAVOR | FLVR_CD | 147-150,155-165 |
| 1048 | 27 | FLAVOR | FLVR_CD | 099,151 |
| 1049 | 27 | FLAVOR | FLVR_CD | 088,154,620-622 |
| 1050 | 27 | FLAVOR | FLVR_CD | 610 |
| 1051 | 27 | FLAVOR | FLVR_CD | 619 |
| 1052 | 27 | FLAVOR | FLVR_CD | 317 |
| 1053 | 27 | PACKAGE TYPE | PKG_TY_CD | 01,02 |
| 1054 | 27 | PACKAGE TYPE | PKG_TY_CD | 00,03,04,05,06,07,08,09,10 |
| 1055 | 27 | SPECIAL LABEL CODE | SPC_LBL_CD | 00,02,03,04,05,06,07,10,11,12,23-28,32 |
| 1056 | 27 | SPECIAL LABEL CODE | SPC_LBL_CD | 01,08,09,21,22,29,30,31 |
| 3017 | 27 | SPECIAL LABEL CODE | SPC_LBL_CD | 33 |
| 3123 | 27 | SPECIAL LABEL CODE | SPC_LBL_CD | 34 |
| 3287 | 27 | FLAVOR | FLVR_CD | 004 |

*Fig. 9L*

| FOOD_CD | COMBO_CD | CAT_CD | TY_CD | FRM_CD | CHAR_CD | FLVR_CD | CLS_CD | PREP_MTHD_CD | PKG_TY_CD. | SPC_LBL_CD | Recipe_CD | PORTION_CD |
|---|---|---|---|---|---|---|---|---|---|---|---|---|
| 271154 | 1017102000001027000000000010541055 | 27 | 0,1,8 | 11,12,13 | | 000,070-316 | | | 00,03,04 | 00,02,03 | 270021 | 6004 |

SYSTEMS AND METHODS FOR DETERMINING NUTRIENTS WITHIN DIETARY INTAKE

CROSS-REFERENCES TO RELATED APPLICATIONS

Not applicable.

STATEMENT REGARDING FEDERALLY SPONSORED RESEARCH OR DEVELOPMENT

Not applicable.

FIELD OF THE INVENTION

The invention relates to techniques for accurately and effectively determining what nutrients people receive in their diets. More particularly, the invention relates to automated systems and methods for analyzing and reporting on dietary intake by merging information from multiple input data sets. The resulting nutritional analysis can help food marketing researchers formulate or reformulate products to address specific dietary deficiencies and improve the overall health of our society.

BACKGROUND AND SUMMARY OF THE INVENTION

Most of us shop carefully for the foods we serve our families. We look for products that are high in nutritional value so our families can have a balanced diet. We are especially careful about the foods we buy for younger and older family members. We understand that eating the right things everyday is important to our health and longevity.

A medium-sized supermarket in America is a wonder of the modern world. Supermarkets offer a wider variety of foods than ever before. There, we can find beef raised in Texas, seafood caught off the coast of Washington State, oranges from Florida, kiwis from New Zealand, other foods from all corners of the globe, and a tremendous variety of prepared and packaged foods. As the wealth of products to choose increases, it becomes more difficult to make healthy and sensible choices for ourselves and our families. Often, we wish we had more guidance.

Advertising is a valuable source of information about new food products we might like to buy and serve to our families. Food product manufacturers are interested in accurately advertising their products and in formulating new products that will appeal to consumers and meet their nutritional needs. For example, there is good evidence that diets rich in whole-grain foods and other plant foods and low in saturated fat and cholesterol may reduce the risk of heart disease. It is important for consumers to know this type of information because it helps them choose and serve more healthful foods.

One way that those involved in food marketing research can ascertain how to improve the diet of a population by better meeting nutritional needs is to collect and record detailed data about what people eat. Food consumption data collected for marketing research purposes provides an in-depth, continuous record of the national population's food intake. The food industry has traditionally used such detailed food records to track consumption of specific branded food items and monitor growth of food categories.

One of the entities that has long been involved in collecting food consumption data is the U.S. Department of Agriculture ("USDA"). The USDA has collected such data since 1965 and most recently conducted a Continuing Survey of Food Intakes by Individuals (CSFII) in 1989–91 and 1994–96. The resulting data sets provide information on two-day food and nutrient intakes by approximately 20,000 individuals of all ages nationwide. The USDA survey data set includes, for example, the kinds and amounts of foods consumed by individuals on each of two non-consecutive days as well as other information (e.g., the source of food, whether the food was consumed at home or away from home, and other information including demographics of the survey participants). The USDA provides the resulting data sets on a CD-ROM along with SAS® statistical analysis programs which read the data files into SAS® and create SAS® data files for statistical analysis. See, for example, brochure, "What's On The CSFII 1994–96, 1998 CD-ROM" (USDA June 2000).

Another useful source of information concerning what we eat is the National Eating Trends® (NET) database generated by the NPD Group of Rosemont Ill. The NPD National Eating Trends® service collects food consumption data from 2,000 households annually (approximately 5,000 people) through the use of 14-day food diaries. The NPD/NET data is continuously collected throughout the year to account for seasonal changes in food intake, and provides detailed descriptions of each food consumed including brand names and descriptive nutritional attributes. This data is collected from a population group that is demographically matched and balanced by age, gender, income, race, household size, female employment status and other factors, to reflect the U.S. Census.

Panelists participating in the NPD survey record food consumed at-home and away-from-home during a 14-day period. The NET database provides consumption patterns and trends of more than 4,000 unique food and beverage products, and identifies a variety of different information including, for example:

the demographics of people who use the products (e.g., gender, age, sex, geographical region, etc.),
household demographics,
number of consumers using the product,
frequency of consumption (trended),
life cycle,
nutritional segments,
appliance used in product preparation,
when and how the product is consumed,
meal occasion associated with the foods consumed,
ingredients used,
toppings and additives added,
foods and beverages eaten alongside product,
whether product was a main dish, side dish, appetizer, dessert or snack, where product is consumed (e.g., in home versus carried from home versus away from home),
other foods and beverages more likely to be consumed by product users.

NPD provides a range of delivery methods to present NET data to its customers. For example, electronic data delivery offers access to trended consumption information on a PC using proprietary NPD Power View® software, a Windows-based system designed for interactive multi-dimensional data analysis. Customized reports and special issue analyses are available to shed light on why consumers do what they do.

The NPD/NET data set is useful for ascertaining what foods American households are eating. The emphasis on household makes sense given that generally, foods are often purchased by one member of a household for the entire household, and meals are generally eaten more or less together within a given household. There is also a practical reason that a single member of the household (e.g., the person in charge of food preparation) generally records the required survey data for the entire household. One of the shortcomings of this emphasis on household data recording is that the diaries record how much of a given food item was served to the entire household, but do not require or permit each household member to record how much of the food he or she consumes individually.

In more detail, the survey form/diary filled out by each household asks the participant to specify how much of the food item was served to the household, how much of the amount served was actually eaten by the household, and who in the household ate the particular food. See, for example, Sample Daily Meal Diary published by NPD Group, incorporated herein by reference. This is a typical procedure for panel surveys to minimize the amount of information recorded and thus increase reliability. One reason for not requiring individual portion size recording is that attempting to require all participants to record how much food was consumed by each over a 14-day period is burdensome and might compromise the accuracy of the recording.

Another potential shortcoming of the NPD/NET dietary intake data set for certain purposes relates to the amount of nutritional information the data set provides. NPD does not attempt to provide detailed nutritional information on each food recorded in its survey. Such detailed nutritional information analysis is typically the work of food research scientists, and is not supplied in the NPD/NET data set. On the other hand, for some food research applications, it would be desirable to provide detailed information concerning the amount of each of over 100 different nutrients (including, for example, individual amino and fatty acids) we consume every day. For example, a company interested in formulating or reformulating a food product to ensure that Americans receive appropriate essential nutrients in their daily diets may want to know how much of each nutrient is consumed each day by each of the various demographic categories of individuals in the United States. Food product manufacturers and providers may also wish to obtain evidence for making advertising claims that their products should be part of your daily diet. Health specialists may wish to analyze nutrient consumption or nutrient consumption trends in the population overall, by demographically-specific segments of the overall population, or by household and/or individual, in order to try and discern correlations between nutrient consumption and disease. Many other applications call for detailed knowledge of the amount of nutrients consumed by every day as well as tracking intake over specific time periods. These issues are not adequately addressed by the NPD/NET data set.

There are good data sources of nutritional analysis for the foods we eat. Several different research entities, including for example, the University of Minnesota, have compiled the nutritional content of many foods. University of Minnesota's Nutrition Data System for Research (NDS-R) software provides detailed nutrient information for more than 18,000 foods, including over 8,000 brand-name products. However, while a wealth of data exists concerning America's eating and consumption habits and corresponding nutritional information, the information resides in a number of discrete data sets developed by different entities (some governmental, some corporate, and some academic). These different data sets are largely incompatible with one another and are generally designed and developed to achieve different overall goals.

The present invention efficiently makes use of this wealth of otherwise-incompatible data by automatically and efficiently integrating plural different data sets. Such capabilities, for example, provide a unique methodology utilizing 14-day food diaries to determine the impact of food consumption patterns on nutrient intake. The resulting integrated database can be analyzed by a conventional statistical analysis package such as SAS® for dynamic analysis and reporting.

In accordance with an aspect provided by an illustrative and exemplary embodiment, a data integration procedure is performed on three independent, special purpose food research related data sets. One data set contains food consumption data based on 14-day diaries. A second data set contains portion size data for a large number of (e.g., over 8,000) different food types. A third data set contains nutrient data for a large number of (e.g., over 18,000) uniquely identified food constituents. The resulting integrated data set can be analyzed using conventional statistical analysis procedures.

In accordance with a further aspect provided by an illustrative and exemplary embodiment, a first data set is analyzed and processed to determine mean age and sex specific serving weights of a certain number of food items. These portion size weights are matched to each food recorded in a second data set representing 14-day food intake. Complete nutrient profiles are assigned to each food in the survey based on a third, nutrient data set. The information from these three data sets is combined in a database, and nutrient intake reports are processed using a conventional statistical reporting interface. This flexible system allows users to categorize the population based on usual consumption of food categories, specific foods and/or specific brands of foods, and to determine dietary differences versus their "non-using" counterparts.

In one non-limiting exemplary and illustrative embodiment, information is integrated from three particular data sources:
    a food intake data set (e.g., multiple years of NPD's National Eating Trends® 14-day food intake data),
        a portion-size data set (which may be obtained for example from multiple years of the USDA's CSFII data set), and
        a nutrient data set (e.g., from a nutrient profile data set provided by the University of Minnesota's NDS-R).

In an example embodiment, the data integration procedure assigns nutrient data and portion size data for each uniquely identified food within the food consumption survey data. This assignment is performed by linking together the three different data sets using a special coding procedure that stores the result as a SAS® data file. SAS® provides an easily accessible and flexible system for reporting the data, performing statistical procedures and producing graphical reports. The data can also be reported for populations selected on any combination of various variables including, for example:
    demographics,
    number of reporting days,
    day of the week,
    meal occasion,
    use of a specific food/foods,
    specific nutrient intake level,
    Recommend Daily Allowance (RDA) level,
    respondent Body Mass Index (BMI),
    other criteria.

There is substantial value to such dietary intake research. For example:

the dietary research results can be used to build credibility in scientific and food policy communities;

the techniques provided by the illustrative preferred embodiment allow the data sets to be explored for new information, trends and themes that are transformational and can stimulate product development, help create marketing programs, and suggest strategies (e.g., BMI and cereal consumption, diet modeling to meet three whole grains per day, etc.). These techniques may also be useful in connection with food product marketing and public relations (e.g., sugar defense, whole grain intake, impact of breakfast cereal on diet, calcium intake, breakfast patterns, cereal portion sizes, eating patterns of children, seniors and other demographic groups, etc.).

The techniques herein may also be useful for new product development and existing product reformulation (e.g., by identifying nutrient needs in a population such as, for example, calcium fortification, folate fortification and enrichment, etc.).

The information provided by the exemplary and illustrative embodiment may also be useful in a regulatory environment to help with claims documentation, policy strategy development, and to provide data for regulatory comments, fortification review and justification.

The information may also be useful to prepare scientific journal manuscripts and abstracts, augment internal and external clinical and laboratory research projects, and for other scientific value.

Additionally, the information provided by an illustrative and exemplary embodiment may be useful to provide data for speeches and presentations, public relations facts, advertising copy, and consumer information.

In accordance with a more detailed aspect of an exemplary and illustrative preferred embodiment of our invention, we use a food descriptor reduction algorithm that reduces the massive amount of food item data provided by a 14-day dietary intake database into a smaller amount of data useful for identifying the nutrients in the foods actually consumed by dietary intake study participants. In accordance with a specific embodiment, a particular advantageous subset of available data fields is used to uniquely identify on the order of over 5,000 food items from over a billion theoretical possibilities. This data field subset may comprise, for example, 8-dimensional coordinates representing food item identification (e.g., type, form, characteristic, flavor, classification, preparation method, packaging type, and special label code). The preferred exemplary and illustrative embodiment combines many of the codes for each type and groups them according to dietary factors that relate to the nutrient makeup of the foods. These combined and grouped codes are ultimately mapped into nutrient values based on portion size and food nutrient content profiles.

In the example and illustrative embodiment, the groupings are performed based on a lookup table using four keys:

a combo (combination) key comprising a unique sequential value identifying a portion of a unique character code, a category code identifying a general type of food group (e.g., cereals, milk, baby food, etc.), a column number pointing to a column in the food intake database, and a column value designating one or more values that apply to this column and category.

In the exemplary and illustrative embodiment, the food descriptor reduction mapping process proceeds by scanning a data reduction table to determine whether the particular food within the dietary intake data has been defined within the table and has a corresponding combination key. Multiple iterative scans yield additional combination keys that may be combined together to provide a combination code for the particular food item identified in the food intake data. The resulting combination code food descriptor is located within a food-portion link data file where foods have been previously defined by combining a portion size data set with a nutrition data set for this particular food descriptor code. If the food descriptor combination code is found within the food portion link file, it is mapped to a simpler unique food designator (for storage space considerations) in the example embodiment. If the code is not found (meaning, for example, that a new food item is being reported in the dietary intake data set), an exception is generated so that a dietary intake scientist can dynamically update the appropriate lookup tables to include the new item. The process can be performed iteratively to interactively define new food items as they are introduced to the population and begin appearing in dietary intake data.

In accordance with another aspect provided by the exemplary and illustrative embodiment, a household master analysis is performed to allow tracking of individuals consumers—even through multiple intake surveys from different time periods. While household-based data is enough for many food research and marketing analyses, individual food and nutrient intake is important for certain other research objectives. The preferred and exemplary illustrative embodiment of this invention is able to track individual person dietary intake from dietary intake data sets that are generally designed on the household level but, as it turns out, include sufficient data to provide individual tracking if that data is handled appropriately.

For example, more accurate dietary intake results can sometimes be obtained by using dietary intake data sets from surveys conducted at different times. Often, such surveys will survey the eating patterns of the same households and the same individuals within the same households. However, households can change in their makeup (e.g., when students go off to college), and different people within a household may serve as reporters/diarists for different survey periods. The exemplary embodiment can determine when the same household and/or individual is included in multiple food intake surveys. In the exemplary embodiment, each individual is assigned a unique individual ID by the preferred embodiment, this individual ID being different from the designator(s) used to code the participant within the food intake data set. Unique individual ID's may then be keyed to the same individuals reporting on different dietary intake surveys to allow for individual long term dietary intake tracking. By analyzing the food intake survey results based on individuals, the exemplary embodiment achieves more accurate results since the eating patterns and dietary intake of an individual reported on multiple different surveys can be weighted as pertaining to the same individual. In addition, significant advantages and flexibility can result from the ability to track individual consumption over an extended time period such as number of years. For example, much valuable information can be obtained by determining how a person's eating habits change with age.

In accordance with a further aspect of an exemplary and illustrative embodiment, data is combined to develop demographic-based (e.g., age and sex) categories for portion size determinations.

In accordance with yet another aspect of a preferred and exemplary embodiment, recipe files are used to extract nutrient information from food descriptors. In more detail, once a particular food item has been identified in the food intake data set, it is desirable to be able to determine what nutrients are obtained from eating that particular food in the particular portion size corresponding to the individual who has consumed that food. Since the food intake survey data set in the example embodiment does not report an individual's actual portion size, portion size information is obtained from a different data set based on age, sex and other demographics of the individual who consumed the food item. Once the food item and portion size are known, the preferred exemplary embodiment uses recipes to determine (or estimate) the nutrients that the consumer obtained from eating that food product.

The nutrient data within the nutrient data set does not necessarily, provide a comprehensive nutrient profile for each and every of the thousands of food products that may be identified. As an example, the nutrient data set may not specify the nutrients obtained from eating a mixture, although the nutrient data set might have complete information concerning constituent components of such foods (e.g., flour, milk, butter, oil and other components of a pancake recipe). In accordance with this aspect of the preferred and exemplary illustrative embodiment, recipe files are maintained and may be used to break down particular identified food items into their component constituent parts. The nutrients within each component part may then be identified from the nutrient data set to provide dynamically an overall nutrient content for the particular food item described by the food descriptor.

BRIEF DESCRIPTION OF THE DRAWINGS

These and other features and advantages provided in accordance with exemplary and illustrative embodiments of the present invention may be better and more completely understood by referring to the following detailed description in conjunction with drawings, of which:

FIG. 1 shows an example dietary intake study system in accordance with a presently preferred exemplary and illustrative embodiment of the invention;

FIGS. 8A–8E are example flowcharts; and

FIGS. 9A–9M show an exemplary progression of data structure modifications involved in an example food descriptor reduction algorithm.

DETAILED DESCRIPTION OF PRESENTLY PREFERRED EXAMPLE ILLUSTRATIVE EMBODIMENTS

FIG. 1 shows an example dietary intake study and analysis system 100 provided by a preferred exemplary and illustrative non-limiting embodiment of the present invention. System 100 determines the impact of food consumption patterns on nutrient intake based on a unique methodology utilizing 14-day food diaries in conjunction with additional data sets providing nutrient and food portion information.

Figure 1A:
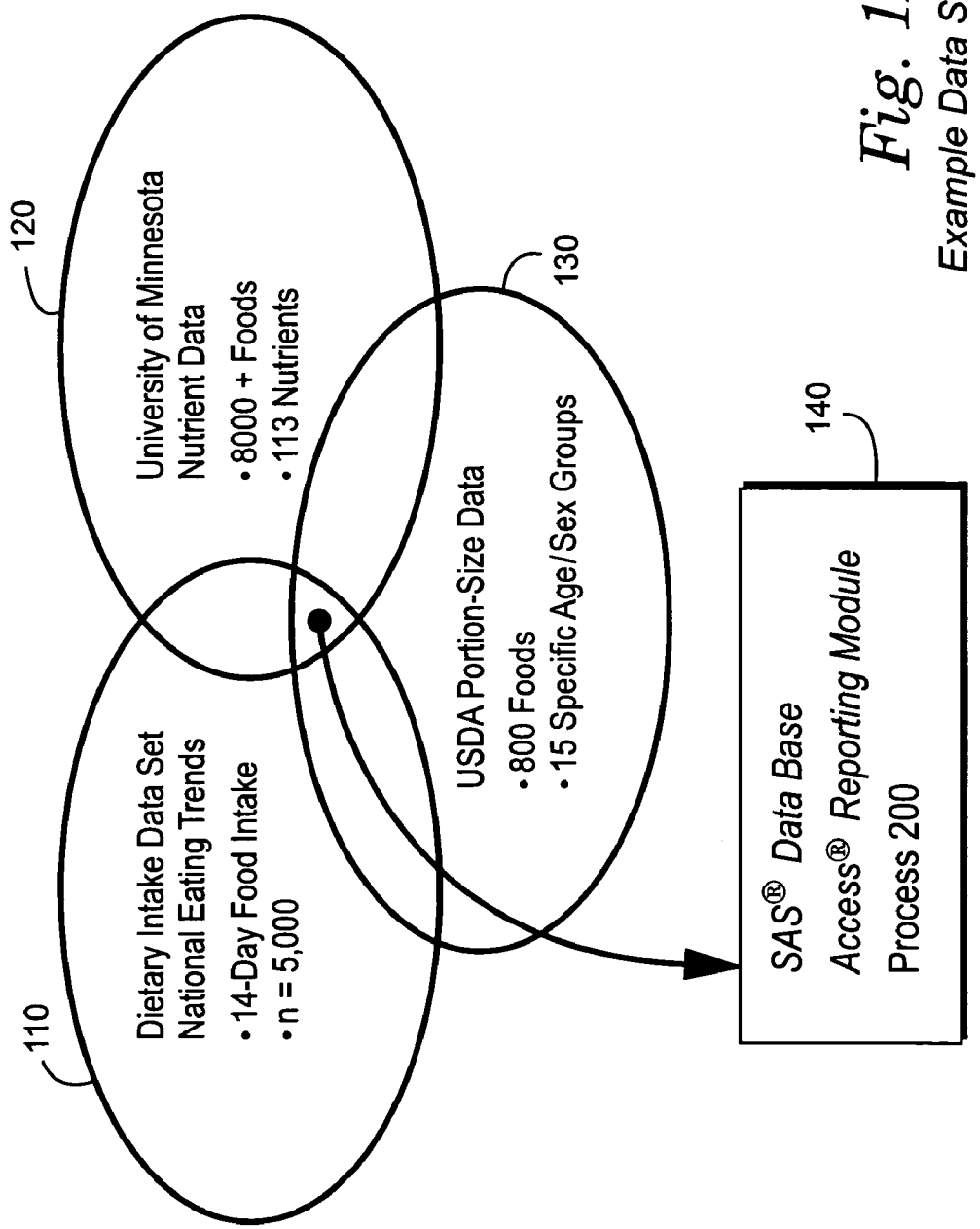
FIG. 1A shows example integration of three different data sets to provide statistical analysis.

As shown in FIG. 1, one input to the overall dietary intake study system 100 of the preferred exemplary embodiment is a 14-day food intake data set 110. This 14-day food intake data set 110 may be, for example, the NPD/NET data set (see FIG. 1A) that results from extensive data collection from a large number of households who record exactly what they have eaten throughout each day of a 14-day period.

In order to enhance the value of the 14-day food intake data set 110 from the standpoint of evaluating and precisely estimating or determining the amounts of over 100 nutrients consumed by each individual survey participant, the preferred exemplary and illustrative embodiment system 100 shown in FIG. 1 includes a data integration mechanism 200 that links information from the food intake data set 110 with information contained within two other data sets, namely a food nutrient data set 120, and a portion size data set 130 in the exemplary embodiment.

Food nutrient data set 120, which is generated by food research scientists, provides detailed nutrient data (e.g., 120 nutrients) for thousands (18,000 or more) uniquely identified foods assigned to on the order of 200 (e.g., 179) specific food groups. One example food nutrient data set 120 is the University of Minnesota's Nutrition Data System for Research (NDS-R). This NDS-R software from the University of Minnesota Nutrition Coordinating Center is used by the preferred exemplary embodiment 100 to assign complete nutrient profiles to each food in the 14-day food intake data set 110. See FIG. 1A.

As described above, the food intake data set 110 used in the preferred exemplary embodiment 110 does not include portion size information for each individual in the survey—rather, portion size is maintained on a household basis but not an individual basis. For our purposes, however, it is desirable to know how much of each nutrient has been consumed by each individual—not just by each household. Many households are often made up of a number of individuals in distinct demographic categories (e.g., older Americans, younger Americans and children; different genders; etc.). Individual-based data can therefore be very important to marketing and health research.

To address this issue with the exemplary food intake data set 110, we link an additional food portion size data set 130 obtained from a different data source e.g., the USDA's Continuing Survey of Food Intakes by Individuals (CSFII). See FIG. 1A. The USDA's survey collects data during two non-consecutive 24-hour days. Dietary collection using 24-hour recall does not necessarily reflect a pattern of "usual" food intake. However, the USDA's data set is actually more complete than the exemplary 14-day food intake data set 110 in certain respects. For example, the USDA's survey requires individuals to record the amount of each food they consumed during the 24-hour survey periods. The USDA data set 130 also provides detailed demographic information (e.g., household size, income, race, age, and sex). The preferred exemplary and illustrative embodiment 100 uses this USDA data set 130 to obtain demographically-based food portion size data. For example, it is possible to statistically determine from the USDA data set 130 that a 34-year old male sitting down to a meal of steak and french fries will probably eat about xxx grams of steak and yyy grams of french fries, whereas a 12-year old female child eating the same meal is likely to eat zzz grams of steak and aaa grams of french fries. System 100 uses this demographically-based portion size information to estimate individual portion size of food intakes recorded in the dietary intake data set 110. System 100 may also include the Pyramid Servings data from the USDA CSFII database using the CSFII food codes.

The amount of data within each of the data sets 110, 120, 130 may be massive. Nevertheless, the preferred embodiment 100 efficiently links relevant portions of these various data sets 110, 120, 130 together using a link/merge data integration process 200 (FIG. 2) to generate a further data set 140 (FIG. 1A). This further data set 140 is structured so it can be statistically analyzed by a statistical analysis process 300 (FIG. 3). Statistical analysis process 300 can respond to individual queries to generate detailed reports 310 indicating individual nutrient consumption patterns. The SAS® statistical package provides an easily accessible and flexible system for reporting the data, performing statistical procedures and producing graphical reports. This flexible system allows the user to categorize the population based on "usual" consumption food categories, specific foods and/or specific brands of foods and determine dietary differences versus their "non-using" counterparts. The data can also be reported for populations selected on any combination of the following variables:

demographics,
number of reporting days,
day of the week,
meal occasion,
use of a specific food/foods,
specified nutrient intake level,
  RDA level,
  respondent BMI.

For example, output data sets 140 can also serve as input files to other analysis software packages (e.g., MindSet®, S-PLUS®, or any other desired analysis process or procedure).

Figure 2:
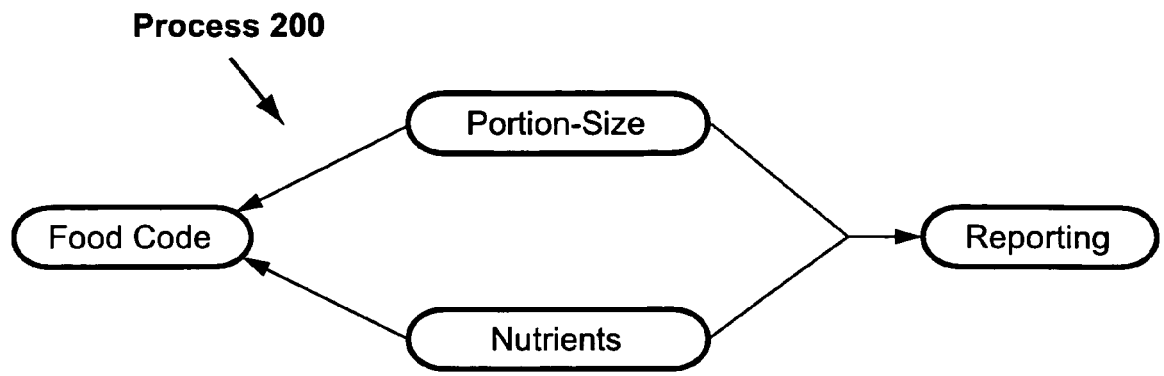
FIG. 2 shows an example data set linkage based on food codes.
Figure 3:
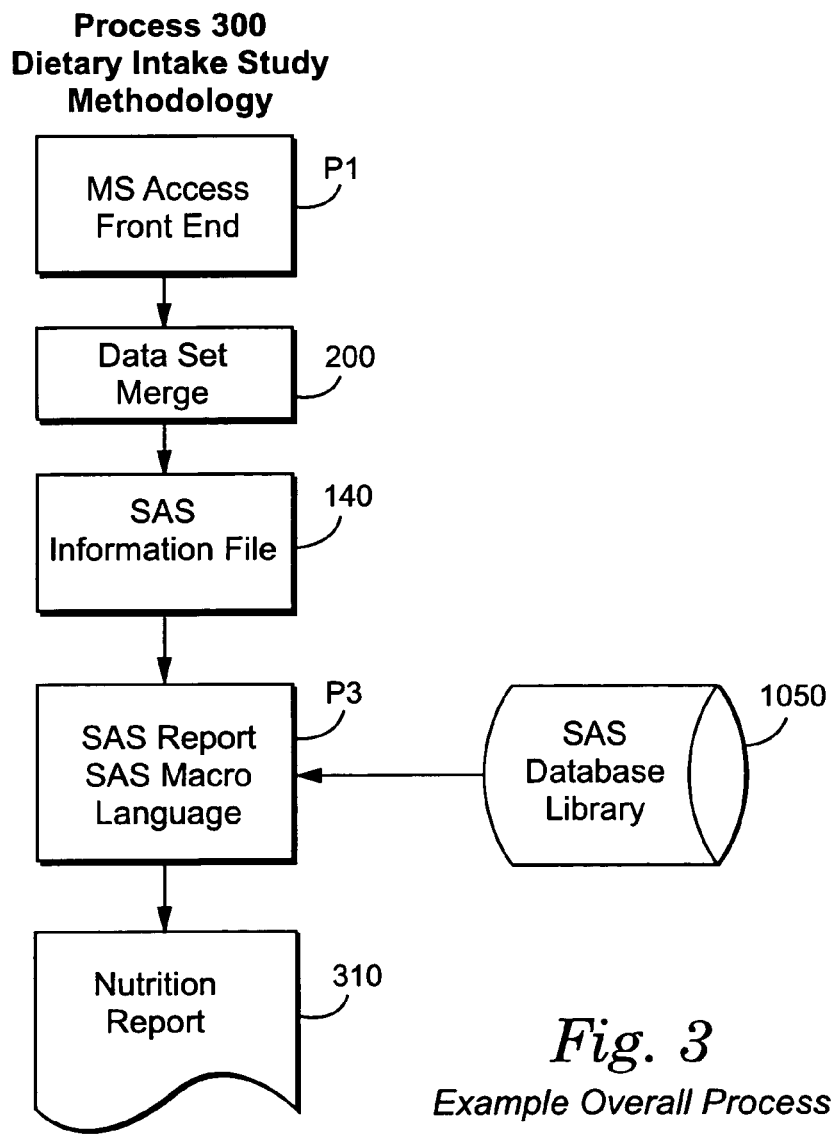
FIG. 3 is a flowchart of an example overall process.

FIG. 2 shows an example technique performed by the link/merge data integration operation 200 to integrate the data from the three data sets 110, 120, 130. In the example embodiment, for each uniquely identified food from the food intake data set 110, nutrient data is generated from the nutrient data set 120 and in addition, sets of portion sizes from the portion size database 130 are assigned. The three data sets 110, 120, 130 are linked together by a special food coding procedure described below, and the resulting integrated data is stored as an SAS® data file 140 for analysis and reporting using conventional statistical analysis tools.

Briefly, the food coding structure used by data integration operation 200 is based on 53 basic food categories in the exemplary embodiment. Each food category includes unique and progressive levels of detail describing the foods in that category. The food coding may include, for example, the following individual coding categories:

Type,
Form,
Characteristic,
Flavor,
Classification,
Preparation method,
Package type,
Special nutritional attributes,
(Other).

FIG. 3 shows an example overall process P performed by the example embodiment 100. In this particular example, a Microsoft Access "front end" or other appropriate application compatible with input databases 110, 120, 130 is used to read in and process the input database contents (FIG. 3, block P1). The data set merge routine 200 is then performed to merge the three data sets 110, 120, 130 into a common information file 140 that can be efficiently and straightforwardly analyzed by conventional statistical analysis tools such as, for example, the SAS® (library 1050). SAS® reporting and macro language may be used in the exemplary and illustrative embodiment to define database queries and specify particular reports and analyses to be run against the resulting output database 140 (step P3) to provide nutrition (and other) reports 310.

Example System Implementation

Figure 4:
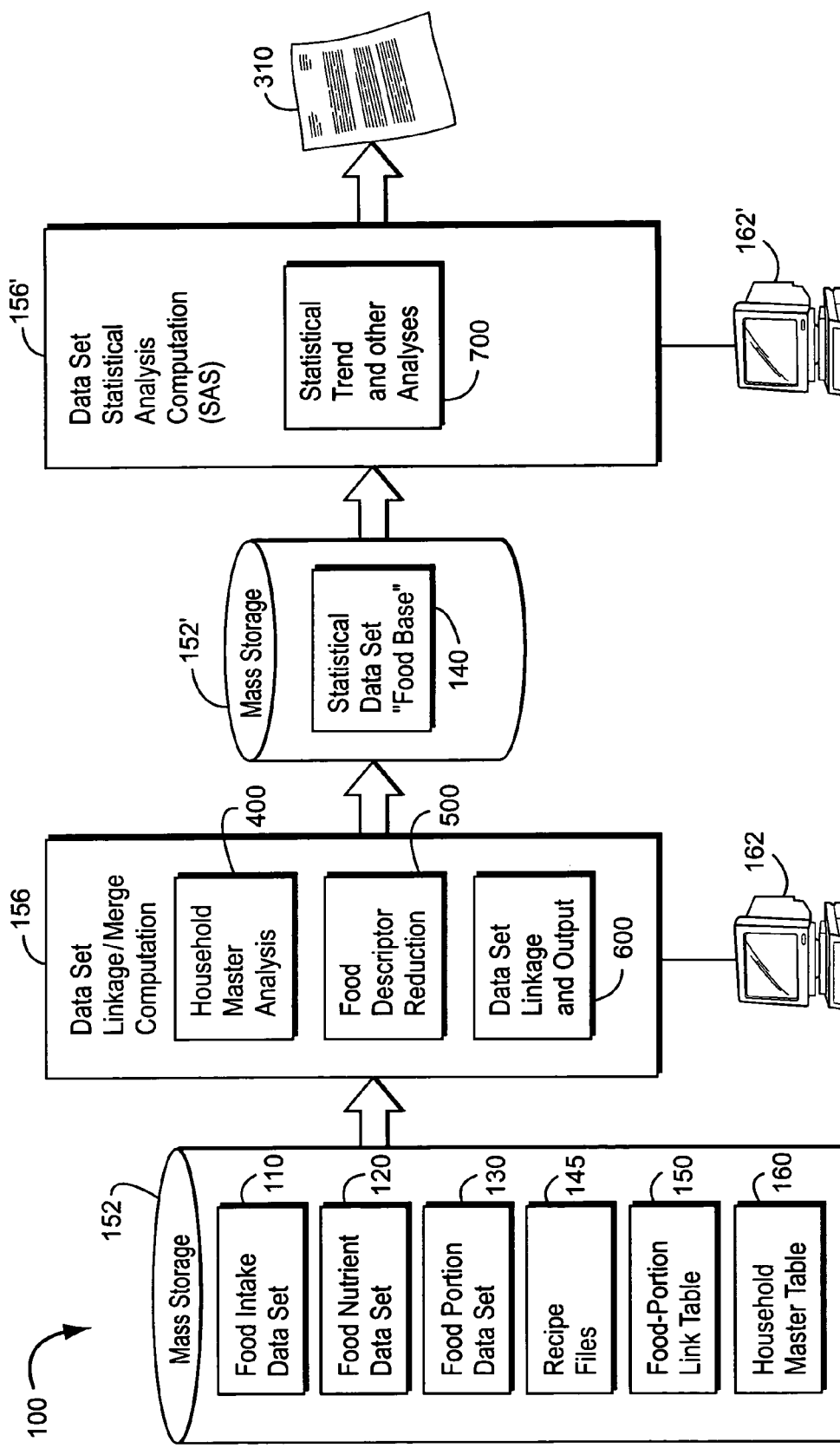
FIG. 4 shows an example more detailed block diagram of an exemplary illustrative dietary intake study computation system.
Figure 5:
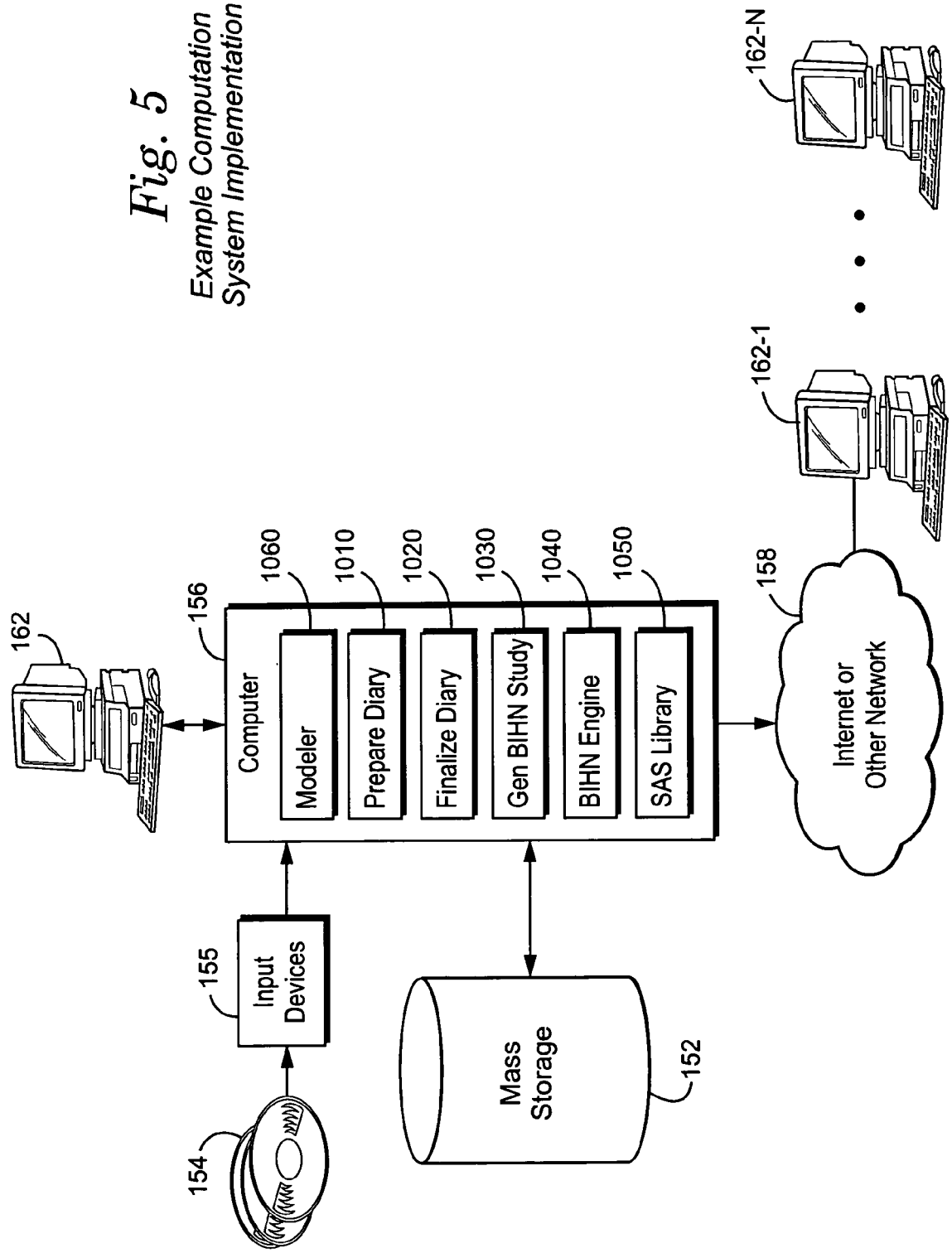
FIG. 5 shows an example illustrative computer system implementation.

FIG. 4 shows an example block diagram of an exemplary and illustrative non-limiting implementation of system 100 shown in FIG. 1. Referring to FIG. 4, the food intake data set 110, nutrition data set 120 and portion size data set 130 are preferably inputted to system 100 and stored on one or more mass storage devices 152. As shown in FIG. 5, the mass storage device 152 (which contains the various data sets 110, 120, 130) can be inputted in a variety of ways including, for example, supplying a portable mass storage device such as a compact disk ROM (154) or other optical magnetic (155) or other mass storage device 152, and/or the data sets may be transmitted in whole or in part over a computer network 158 such as the Internet.

In the example embodiment 100, mass storage device 152 in FIG. 4 (which may comprise one or an array of individual magnetic disk drives, for example), also stores additional data structures including, for example, a recipe file 145, a food-portion link table 150, a household master table 160 and other data structures (e.g., 135). These data structures 145, 150, 160 in the exemplary embodiment are generated and/or updated by system 100 and are used in the data integration process 200.

As also shown in FIG. 4, a computation block (which may be implemented by one or a number of different computers such as mini-computers, main frame computers and/or personal computers) perform certain data analysis and processing routines and procedures including, for example:

household master analysis 400,
food descriptor reduction 500, and
data set linkage and output 600.

These various processes 400, 500, 600, under interactive control of one or more users via display workstations 162, generate a statistical data set called "food base" 140 that represents integrated data obtained from the three input data sets 110, 120, 130. The computation block 156 outputs this statistical data set 140 for storage on the same or different mass storage device 152'. If desired, this statistical data set 140 may be transported to a different location via optical disk 154, 155, network 158 or otherwise for further manipulation and analysis.

In the example embodiment, the same or different computation block 156' (e.g., a personal computer) performs statistical, trend and other analysis 700 on a statistical data set 140 in response to user commands (e.g., inputted via one or more work stations 162) to generate reports 310. These reports 310 may be printed on a printer, displayed on a work station 162', and/or transmitted (e.g., via e-mail, web pages, or otherwise) over network 158.

As is also shown in FIG. 4, the exemplary system 100 includes an additional Health Focus data set 135 that is linked directly to the households defined within the food intake data set 110 (and thus to household master table 160). The Health Focus data set 135 may be supplied, for example, by the NPD Group. The Health Focus data set 135 allows users of system 100 to study attitudes about health and their correlations to dietary intake at a household level. Note also that in the exemplary embodiment, the food intake data set 110 preferably comprises the results of several different surveys (i.e., a survey about a decade old as well as a more current survey) in order to provide information on long-term trends.

Referring to FIG. 5, in one specific exemplary implementation, computer 156 executes a number of specific processing routines in order to implement the data integration process 200 described above. In this particular example, computer 200 may execute, for example:

- a "prepare diary" routine 1010 and a "finalize diary" routine 1020 that processes the food intake data set 110 (e.g., to perform the data reduction process 500);
- a "genBIHNstudy" routine 1030 that generates the statistical data output set 140;
- a "BIHN engine" routine 1040 that further processes and completes the output data set 140; and
- a "SAS® library" routine 1050 (which may be executed on the same or different computer 156 and may include alternative analyses based on other statistical or other packages) that analyzes the output data set 140 to provide reports and other analysis results on demand.

As also shown in FIG. 5, exemplary system 100 may include a modeling aspect in the form of a modeler 1060 that has the capability of modeling nutrient data, portion data and recommended daily allowances. This modeling capability can enhance the operation of exemplary system 100.

Example Software Architecture

Figure 6:
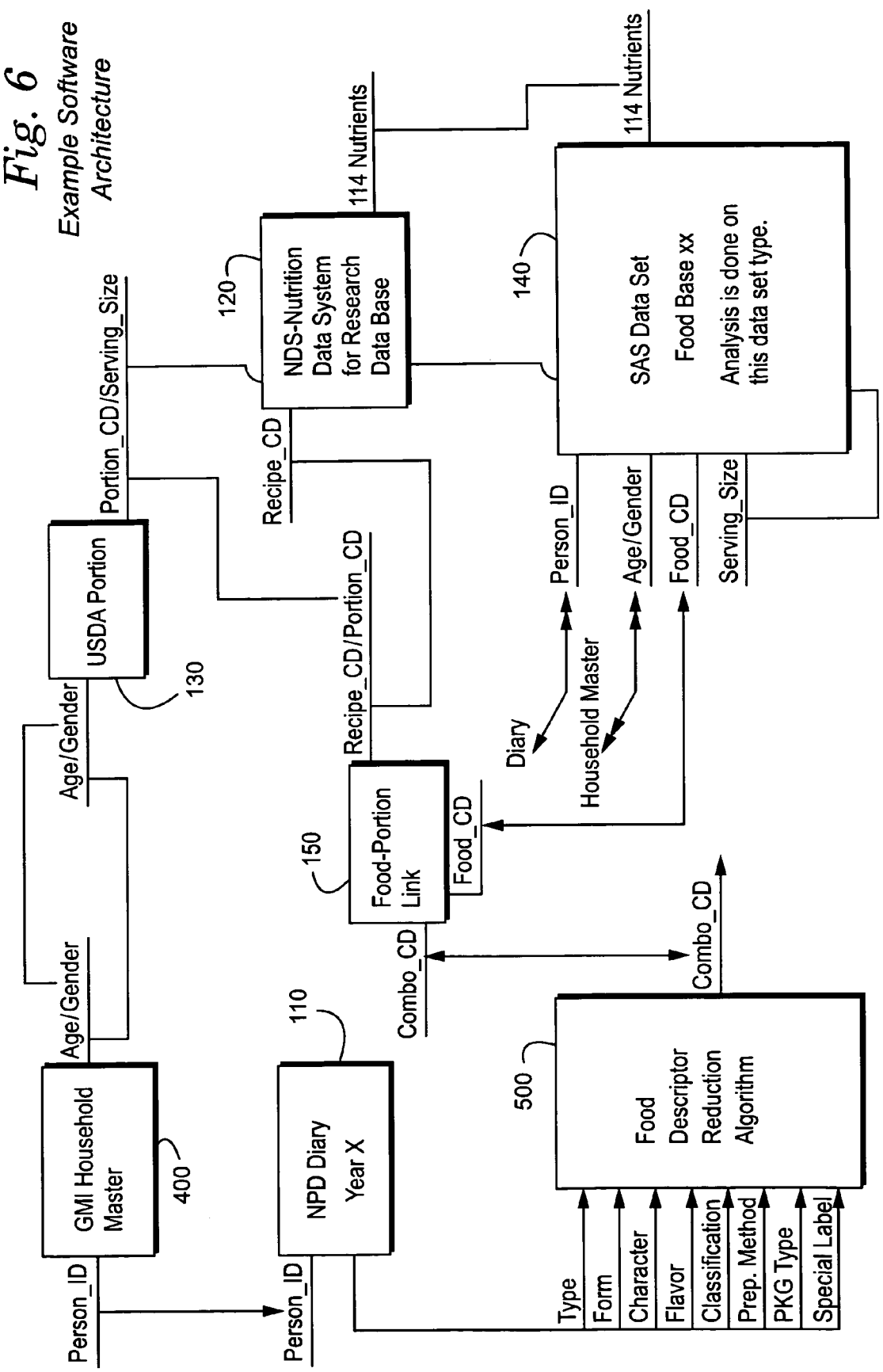
FIG. 6 shows an example software architecture.

FIG. 6 shows an example software architecture diagram indicating how the FIG. 5 routines process the various information within data sets 110, 120, 130 in the exemplary and illustrative embodiment. In the example embodiment, the household master routine 400 meanwhile processes the dietary intake data set 110 to resolve individual dietary consumption records therefrom (i.e., by resolving household into individuals, and matching up individuals duplicated in different surveys within the dietary intake data set 110 from different time periods to unique individual IDs assigned by system 100 so that the same individual is not counted twice but rather has all of his or her dietary intake data from different surveys considered as being associated with the same person—irrespective of whether the individual acted as reporter on only some but not all surveys from his or her corresponding household).

In this particular example, the dietary intake data set 110 is processed by the food descriptor reduction algorithm 500 which codes each food in the intake data set 100 eaten by a given individual based on particular fields within the dietary intake data set. As mentioned above, in the specific exemplary and illustrative but non-limiting embodiment, those fields used for food coding in the exemplary embodiment define an 8-dimensional coordinate system specifying the following food item parameters:

- food type,
- food form,
- characteristic,
- flavor,
- classification,
- preparation method,
- package type,
- special label.

The food descriptor reduction algorithm 500 generates a combination code ("combo_CD") that is provided as an input to the food-portion link table 150. Food-portion link table 150 in the exemplary embodiment links particular identified food items with corresponding recipe information from recipe file 145 and with corresponding food portion size information obtained from the portion size data set 130.

As the exemplary data integration process 200 steps through the dietary intake data set 110 dynamically resolving individual identifiers with the household master routine 400, demographic information (primarily age and gender in the exemplary embodiment) are extracted from the dietary intake data set 110 for the corresponding individual and applied to the portion size database 130. The portion size data set 130 outputs a portion size code that indicates, on a statistical basis, what size portion of the particular identified food item the particular individual (i.e., based upon the individual's demographic information) is likely to have consumed. This portion size information is used in two ways in the exemplary and illustrative embodiment. In particular, the portion size information is applied to the food nutrient data set 120 in order to allow eventual calculation of the amount of food nutrients consumed (note that the total amount of consumed nutrient is a function of both what food was eaten and how much of that food was eaten). Additionally, the portion size information obtained from portion size data set 130 is applied as an input to the food-portion link table 150 as mentioned above. The food portion link table in the example embodiment uses the portion size information and recipe information from recipe file 145 and the combination code to generate a food code to output to the output data set 140.

In the example embodiment, the recipe code obtained from recipe files 145 is used to determine each one of the particular constituent ingredients present within the food item that was consumed as well as the proportional amount of each ingredient that was present within the particular food item. The recipe files 145 are developed in the preferred exemplary and illustrative embodiment to accurately reflect each nutritionally significant ingredient within each of several thousand foods that people commonly eat. In some cases (e.g., when dealing with brand name prepared food products), the recipe files 145 will extremely accurately specify each of the food item ingredients and proportion of each. In other instances (e.g., homemade foods such as pancakes or homemade soup), the recipe files may be less accurate and may instead rely on more detailed ingredient breakdowns provided by the dietary intake data set 110. In any event, the purpose of recipe files 145 is to as accurately as possible resolve individual food items identified in the dietary intake data set 110 into their respective individual nutritionally-significant constituents and corresponding relative amounts of each.

The exemplary embodiment uses this recipe information in conjunction with portion size information (e.g., in a straightforward mathematical multiplication or other scaling) to obtain the amount (e.g., in grams or other convenient quantity units) of each nutritionally-significant constituent within the food item that was consumed. This constituent identification and quantity information is used to index the nutrition data set 120, which generates a corresponding list of nutrients within that constituent component in the amount of same. The nutrition data set 120 outputs this nutrient list/quantity to the output data set 140.

Data set 140 also receives, in the exemplary embodiment, the person identifier from the dietary intake data set 110—allowing tracking of consumption trends on an individual basis. The output data set 140 also receives demographic information (e.g., age, gender, and other factors) corresponding to the nutrient profile to facilitate demographic-based analysis. The output data set 140 also stores the food code to identify the particular food involved, and may also store serving size information obtained from the portion size data set 130.

Figure 7:
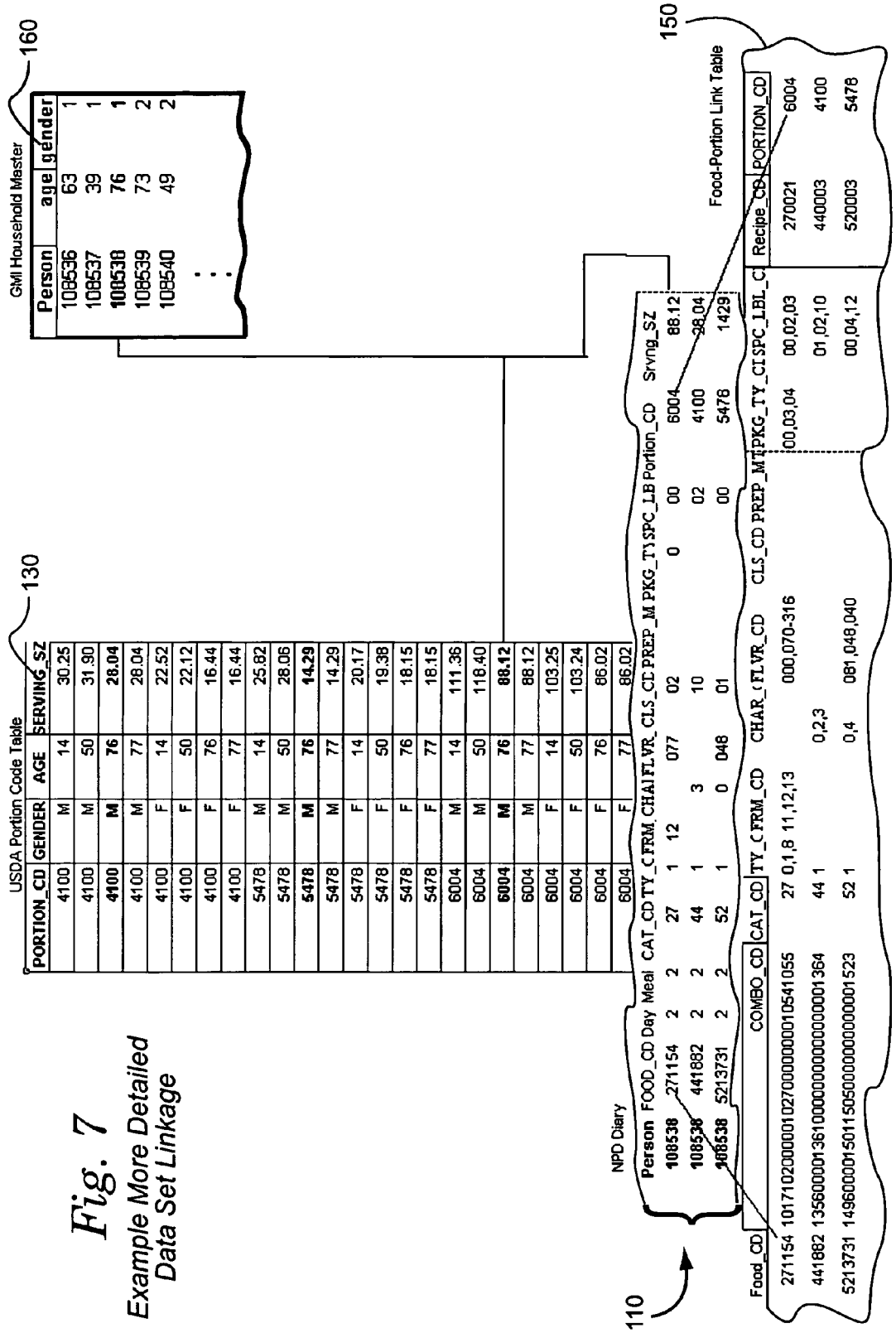
FIG. 7 shows an example detailed data set linkage diagram

FIG. 7 is an example diagram showing a particular non-limiting but exemplary and illustrative data set linkage. This FIG. 7 diagram illustrates exemplary links between an example household master table 160, the dietary intake data set 110, the portion size data set 130 and the food portion link table 150. In the exemplary and illustrative embodiment, a (human) dietary research scientist adds the portion code to the food portion link table 150 when a particular recipe is finalized. The portion code (portion_cd) is then added to the diary 110 when the food descriptor reduction algorithm 500 routines are executed. Once this is finished, the serving sizes are added to the diary 110 based on the age, gender, and possibly other demographics of the person.

As shown in FIG. 7, the exemplary household master table 160 may include individual person identifiers (assigned sequentially in the exemplary embodiment, although other methods of assigning personal IDs may be used if desired) and also identifying age and gender (and possibly other demographics if desired) of that person. The person ID of the household master file 160 once assigned is incorporated into the individual dietary intake records within dietary intake database 110 (e.g., by actually writing the person ID into each associated record) in order to associate the dietary intake information within data set 110 with the person ID assigned by exemplary system 100. In this way, system 100 personalizes the dietary intake data set 110 to better reflect individualized information—and in the process, is able to assign the same person ID in cases where the same person participated in multiple dietary intake surveys.

The exemplary system 100 looks primarily at the eight dimensions of food coordinate information described above as shown in this exemplary fragment of a dietary intake data set 110. The exemplary system 100 reduces various information within the eight fields of the dietary intake data set 110 into a 32-digit combination code that is then used to index into a food-portion link table that uniquely defines thousands of different foods and associates them with corresponding recipes within the recipe file 145 and corresponding portion information stored in the portion size data set 130. In this way, the food-portion link table 150 establishes linkages between the dietary intake data set 110 and the portion size data set 130. Once the portion size for the demographics of the particular individual (as recorded in the household master file 160) and particular food item are known, it is possible to obtain a statistically accurate portion size from the portion size data set 130. System 100 then uses this portion size information along with the recipe information to obtain nutrient amounts from the nutrient data set 120.

Exemplary and Illustrative Process Flow

FIGS. 8A–8E show an example overall process flowchart of steps performed by the example preferred embodiment. In the example shown, the process flow begins at a "start" bubble shown in FIG. 8A (block 1100). The first step in the exemplary embodiment is to read in a dietary intake record from data set 110 and add a corresponding unique person identifier to an incoming dietary intake household file 1102 for a particular year (block 1104). As explained above, the dietary intake data set 110 is generally organized by household although it also includes individual demographic information for each person in the household.

Figure 8B:
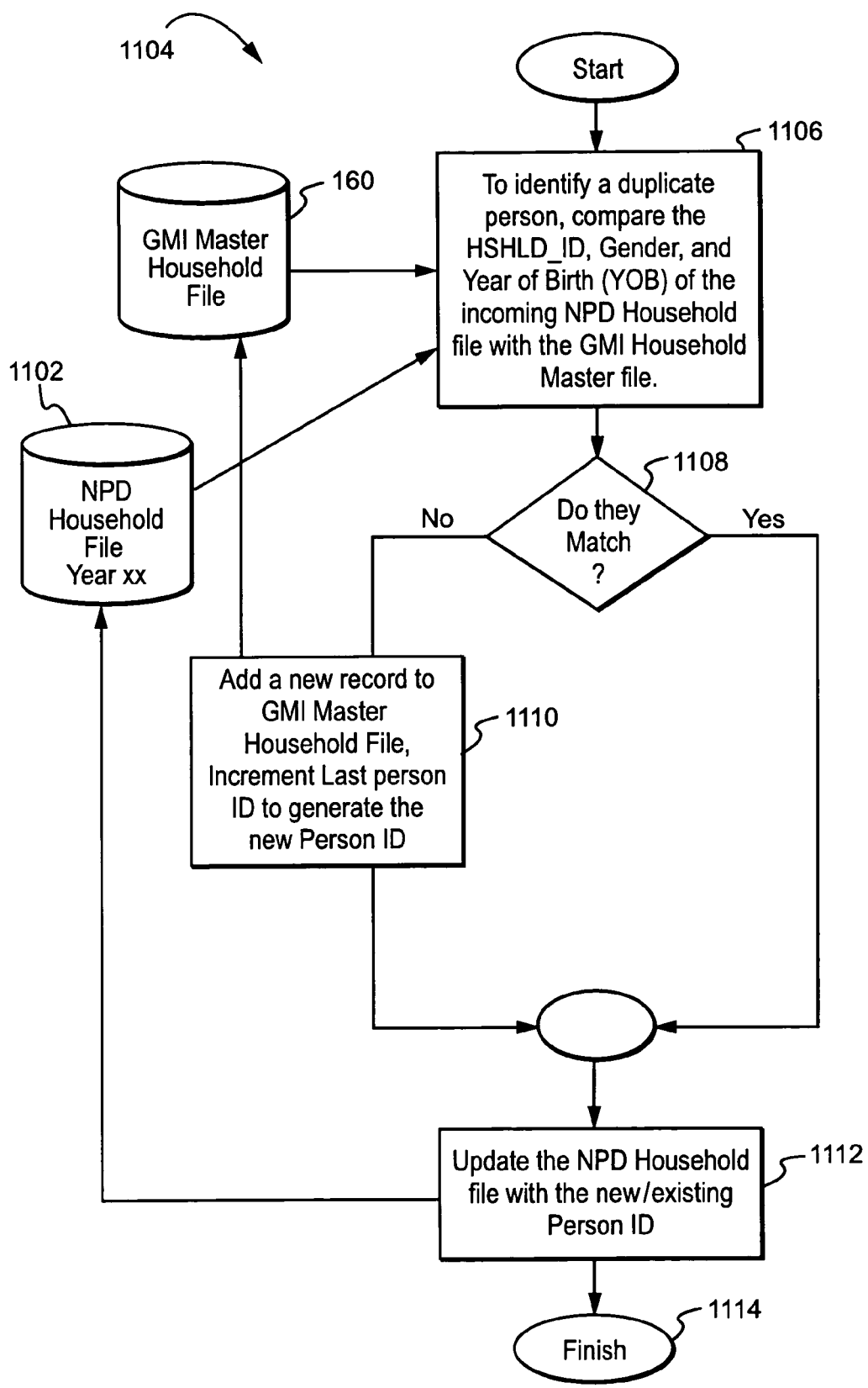

FIG. 8B shows an example more detailed flowchart of steps performed by the FIG. 8A block 1104. In this exemplary embodiment, system 100 creates its own unique identifier for each individual in order to more accurately track individuals. The exemplary dietary intake data set 110 is more concerned with a household level. For example, different household members can act as reporters during different diary survey time periods within the exemplary dietary intake data sets—maintaining a high degree of accuracy on the household level but possibly causing problems if one is trying to identify food consumption on the individual level. The exemplary embodiment of system 100 provides the FIG. 8B routine 1104 to actively identify individuals who have participated in the dietary intake survey in prior years, and to assign them the same preexisting ID (e.g., a sequential or other value). In the example embodiment, individual consumption data provided within data set 110 corresponding to the same person for different survey time periods will thus be matched and recorded within output data set 140 under the same unique individual identifier to allow intake and nutrition tracking on an individual person level. Routine 1104 adds new individuals to the household master file 160 as needed, and new identifiers are generated for them as well on an as-needed basis.

Referring to FIG. 8B, the preferred exemplary embodiment identifies a duplicate person by comparing the household identifier, gender and year of birth of the incoming dietary intake data set 110 record with the contents of exemplary embodiment household master file 160 (block 1106) (note that year of birth is used rather than age since age is relative to the year the survey was conducted). If there is a match ("yes" exit to decision block 1108), then there is no need to update the master household file 160 with a new identifier. However, if there is no preexisting identifier within the master household file 160 corresponding to this individual ("no" exit to decision block 1108), the preferred exemplary embodiment adds a new record to the master household file 160 and increments a "last person identifier" counter to generate a new unique person identifier—thereby assuring that each individual within the output data set 140 will have a corresponding unique identifier (block 1110). In the example embodiment, routine 1104 updates the dietary intake data set household file 1102 for that particular year with the new/existing person ID (block 1112), and returns (block 1114).

Referring once again to FIG. 8A, once the routine 1100 is satisfied that the incoming dietary intake household file 1102 includes a unique person ID corresponding to each person associated with a dietary intake record, the exemplary embodiment combines and cleans dietary intake "in home" and "away from home" diaries 1116, 1118 to create a common diary corresponding to an individual (block 1120). The exemplary and illustrative embodiment 100 uses these diaries 1116 to identify and filter out people who have not reported consumed food items correctly. This is something that is not automatically or generally included within the dietary intake data set 110. The example embodiment 100 identifies the meals that are reported as consumed and yet contains certain fields that are null (i.e., failing to specify what was eaten at that particular meal). In the example embodiment, in home non-reported meals are coded as one particular value (e.g., "10") and away from home non-reported meals are coded as another particular value (e.g., "12"). These records are filtered out later in the process. Non-reported meals are differentiated from valid skipped meals—which the preferred exemplary embodiment 100 does track for certain analysis.

Figure 8C:
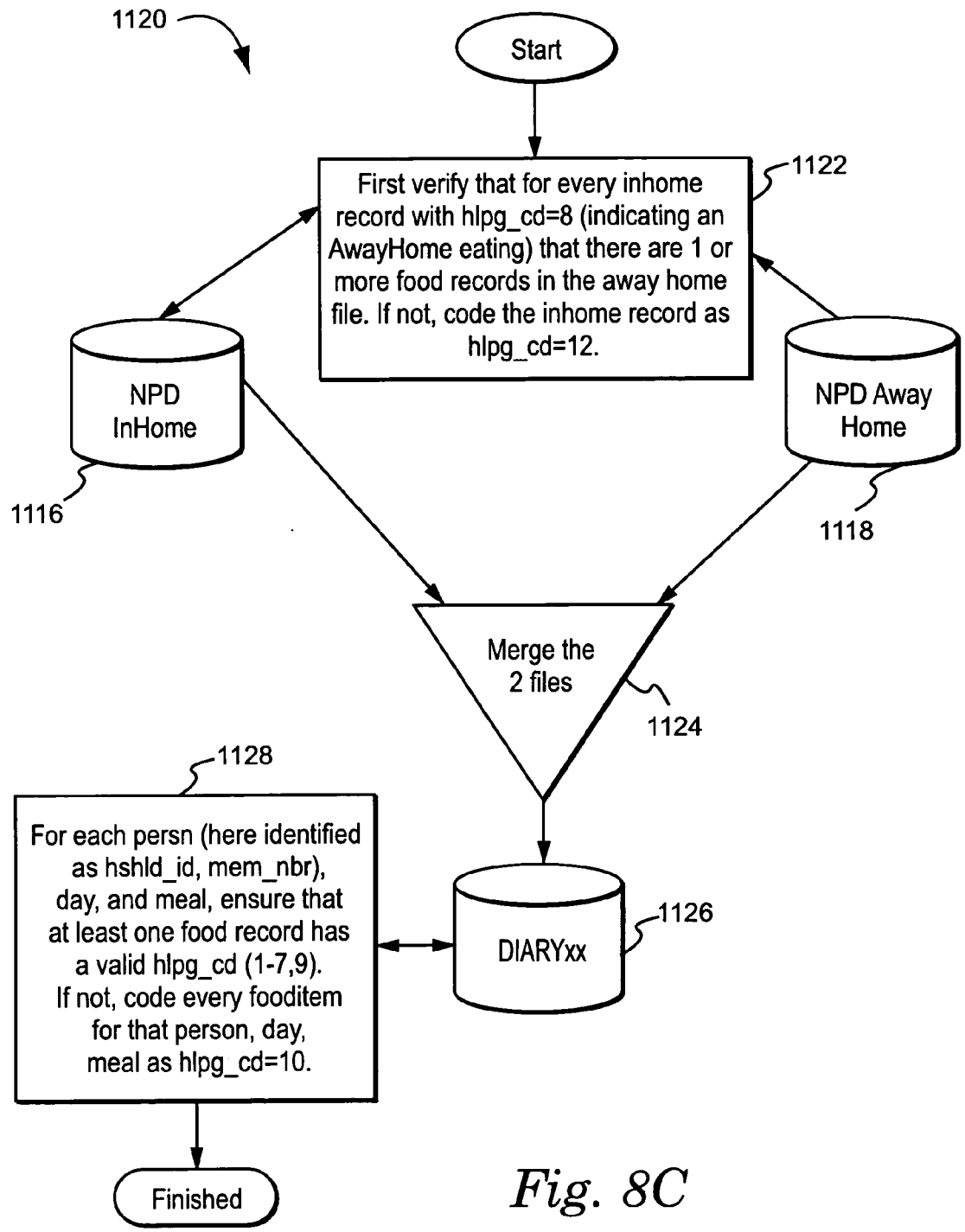

FIG. 8C shows a flowchart of exemplary and illustrative steps performed by the diary creation routine 1120 of FIG. 8A. Referring to FIG. 8C, the example embodiment first verifies that for every in home record with a particular value indicating an away home eating, that there are one or more food records in the corresponding away home file 1118 (block 1122). If this is not the case, then the example embodiment 100 codes the in home record with a particular coding indicating a non-reported meal (block 1122). The in home and away from home files 1116, 1118 are then merged (block 1124) to create a diary file 1126 for the corresponding time period. The example embodiment analyzes the diary file 1126 to determine for each person (here identified by household ID, member number) the day and meal in order to ensure that at least one food record has a valid helping code (block 1128). If no food record has a valid helping code, then each food item within the record corresponding to that person, day and meal is coded to indicate an in home non-reported meal (block 1128). This data processing removes erroneous (i.e., non-reported) meal records in order to increase the accuracy of the resulting output data set 140.

Referring once again to FIG. 8A, once the food intake diary 1126 has been created, the exemplary embodiment matches diary records with household records to acquire the personal identifier, age, gender and possibly other demographic information from the updated household table 1102 (block 1130). The next step the exemplary embodiment of process 1100 performs is the food descriptor reduction algorithm 500. In this example embodiment, this involves generating, for each record within the diary file 1126, a code value that either identifies an existing food item (i.e., from the food portion link table 150) or a new food item (i.e., an identified food item not yet defined within the food-portion link table 150).

In the example embodiment, the reduction routine 500 allows preferred exemplary embodiment to tie together the dietary intake data set 110 and the portion size information within data set 130. In the exemplary embodiment, rather than generating all possible combinations (eight factorial), the reduction algorithm 500 is able to find an existing food code or to generate a place for a new food code using only a few thousand records (e.g., on the order of 2000). Thus, reduction algorithm 500 substantially reduces the total number of different food items that the dietary intake data set 110 can theoretically define into a much smaller, more practical number of different food items commonly eaten by most people.

Figure 8D:
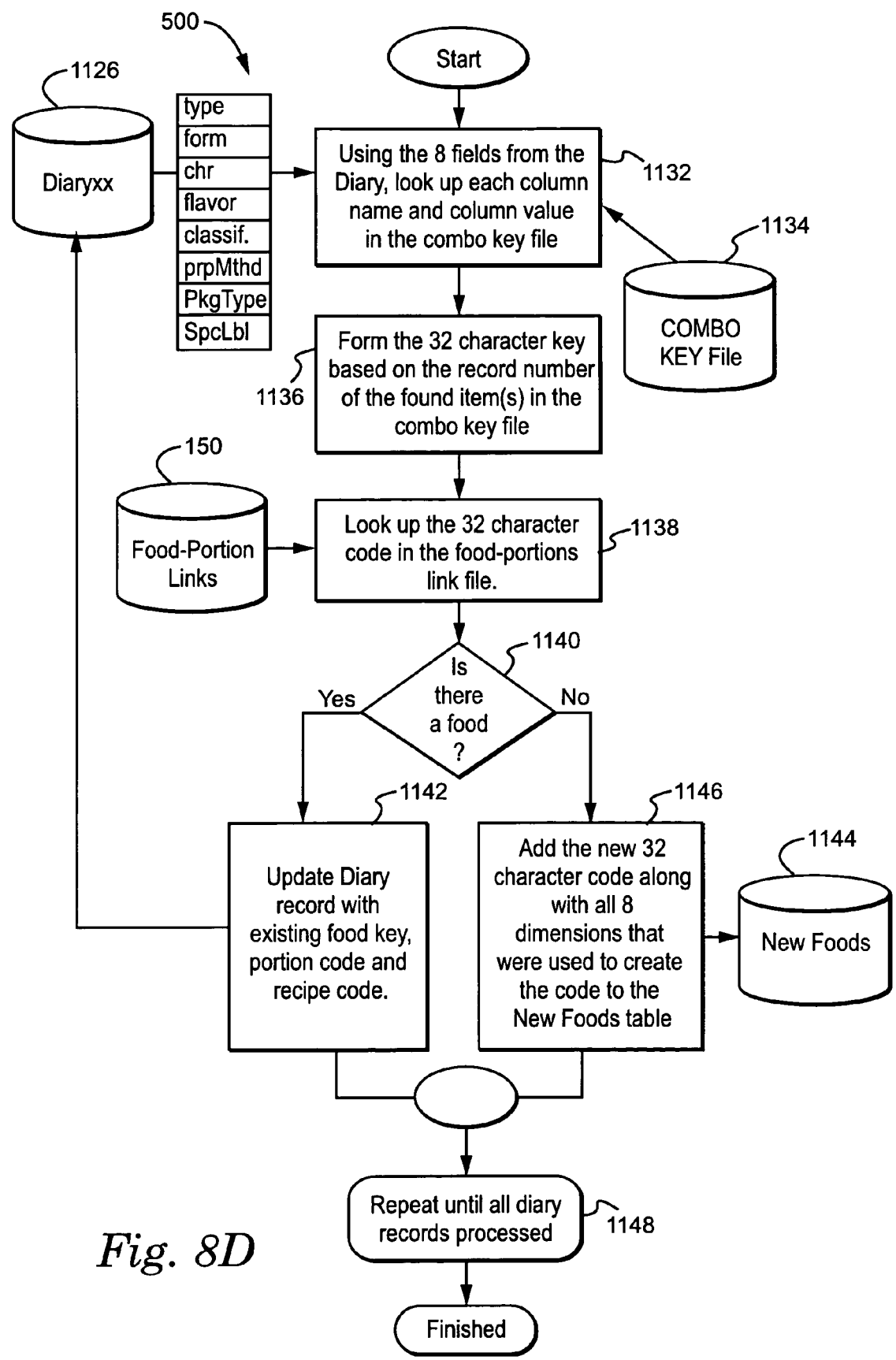

FIG. 8D shows example steps performed by the food descriptor reduction algorithm 500 of the illustrative embodiment. In this particular example, using eight particular fields from the dietary intake data set 110 (i.e., Type, Form, Characteristic, Flavor, Classification, Preparation Method, Packaging Type, Special Label Code), the exemplary embodiment identifies uniquely over 5000 different food items (block 1132). In the example embodiment, each of these various fields contains a numeric code from 1–3 characters long. The exemplary embodiment combines many of the codes for each type and groups them according to several dietary intake factors which relate the nutrient makeup of the foods that will ultimately be mapped. These groupings are then stored in the food-portion links lookup table 150.

In more detail, a COMBO KEY file 1134 is maintained that correlates combination key information with column name and column value information. In the example embodiment, the COMBO KEY may be a unique sequential four-digit number which identifies one-eighth of a unique 32-byte character code. The column name field may specify the actual column name in the dietary intake data set 110. The column value field may provide one or more values that apply to this particular column and associated food category. A category code may also be maintained that specifies certain number (e.g., 53) unique category codes that identify a general type of food group (e.g., 10=cereals, 3=milk, 53=baby food, etc.).

As an example, assume the following values:

| | |
|---|---|
| Type: | 0 |
| Form: | 12 |
| Characteristic: | 0 |
| Flavor: | 249 |
| Classification: | 2 |
| Prep Method: | 0 |
| Package Type: | 3 |
| Special Label: | 34 |

Assume further the following two rows exist within the COMBO KEY file 1134 identified above:

| COMBO_KEY | CAT-CD | CMBNTN-COL | COL_NM | CMBNTN_VAL |
|---|---|---|---|---|
| 299 | 10 | FLAVOR | FLVR_CD | 249 |
| 3243 | 10 | SPECIAL LABEL CODE | SPC_LBL_CD | 34 |

In the example above, the reduction algorithm 500 would take each dimension and scale the cmbntn_val column for the value given for the particular category code and column name. If found, the COMBO KEY would be converted to a four-character string and inserted into the appropriate portion of a 32-character code as follows for example:

| 0000 | 0000 | 0000 | 0000 | 0000 | 0000 | 0000 | 0000 |
|---|---|---|---|---|---|---|---|
| type | form | characteristic | flavor | classification | prep. mthd. | pkg type | special label |

Not all dimensions are required to uniquely identify a food. The algorithm is flexible enough to assign 0 (null) to column names that are not found in the scan in the preferred exemplary embodiment.

Thus, as described above, if one scanned for cmbntn_val=249, for col_nm=flvr_Cd and category code=10 in the example combo key file 134 fragment shown above, the algorithm will find a corresponding unique combo_key equal to 299. The algorithm in the exemplary embodiment converts that value to "0299" to provide a four-digit value, and inserts it into the fourth octet which corresponds to flavor. Next, SPC_LBL_CD=34 is found for category=10, and that unique combo key for that record is converted to string "3243" and inserted into the eighth octet. In this particular example, these are the only two dimensions that are required for this particular food item since no other column names for this category code are found (not illustrated) so that the corresponding 32-character code is then defined as:

00000000000002990000000000003243

In this way, the data reduction algorithm 500 may iteratively access the combo key file 1134 to build a 32-character code that packs the various food item attributes described above and uniquely identifies the particular food item. This technique identifies all foods in the intake data set 110 which efficiently eliminates the need to represent unused food item combinations within the food-portion links file 150—as explained below.

In still more detail, FIGS. 9A–9L show an exemplary progression of data structures process as described above. FIG. 9A shows an exemplary excerpt from a food diary 1126 (not all fields are displayed for lack of room). When the exemplary system 100 begins to process this diary 1126 information a first record is pointed to (as indicated by the highlighting on the FIG. 9B), and that record is then read in and the steps 1132, 1136 of FIG. 8D are performed to generate a food code which is preferably written back to the diary 1126 (see FIG. 9C). FIG. 9D shows the exemplary diary 1126 excerpted after the FIG. 8D routine 500 is performed for all of the records in the excerpt.

FIG. 9E shows an example combo key file 1134 that is used by FIG. 8D block 1132 to translate the eight dimensions describing a food item from the dietary intake data set 110 to a 32-character unique code that will map to the food portion link table 150. The example shown in FIG. 9E is an excerpt of the records returned by the combo key file 1134 for an exemplary diary entry as shown in FIG. 9F having a category code of a particular value (in this case "27"). FIG. 9F shows the relevant data fields highlighted. In this particular example, the key columns are TY_CD (Type), FRM_CD (Form), FLVR_CD (Flavor), PKG_TY_CD (Packaging Type), SPC_LBL_CD (Special Label). The other highlighted columns are irrelevant for this particular category code.

FIG. 9G shows an example where the Type (TY_CD=1) is included in an CMBNTN_VAL in a particular record number 1017. This is an example of parsing the type column name to create a combination key based upon the "Type" information. FIG. 9H shows a similar example where another combination key ("1020" in this particular example) is created based on the "Form" information within the diary 1126. FIGS. 9I, 9J and 9K show additional examples that create combination codes for flavor, package type and special label coding respectively. Note that these are only examples, and that a different diary entry will generate different combination codes based upon the particular values of the eight exemplary food descriptor dimensions.

In this example, the resulting 32-digit food code (obtained by concatenating the various combination codes together in a particular order) is defined as:

1017 1020 0000 1027 0000 0000 1054 1055

The matching records that create the above combination key are highlighted in FIG. 9L. FIG. 9M shows the corresponding diary entry 1126 that is returned with the 32-digit combination code obtained by the above exemplary food descriptor reduction process 500.

Once the data reduction algorithm has derived the 32-character key based on the record number of the found item(s) in the combo key file 1134 (block 1136), the reduction algorithm looks up the 32-character code in the food-portions line file 150 (block 1138). In more detail, the data reduction algorithm 500 does a scan of the food-portion links file 150 where foods have been previously defined (i.e., by previous operations of system 100) by combining the portion size data set 120 with the nutrition data set 130 for this 32-character code. If found ("yes" exit to decision block 1140), then the food diary record 1126 is updated with the existing food key, portion code and recipe code (block 1142) obtained from the food-portion link table 150 (see FIG. 7). In the example embodiment, the food-portion link table 150 provides mapping to a simpler unique long integer number ("food_cd") for storage space consideration. Routine 1100 also increments a counter to track the number of times this particular food item is used in the diary 1126. The diary 1126 record is also updated with the food_cd value and the portion code from the portion size data set 120 for later merging into the final output data set 140.

If a 32-character food code is not found in the food-portion link file 150 ("no" exit to decision block 1140), then the new 32-character code is added along with all eight dimensions (i.e., type, form, characteristics, flavor, classification, preparation method, package type, special label) identifying the food item, into a "new foods" table 1144 (block 1146). The overall process shown in FIG. 8D is repeated until all records within diary 1176 have been processed (block 1148).

Generally, if the 32-character code is not found, then an exception record is written and one of two things will happen. First, if the 32-character code is not found due to a new and previously undefined value within the dietary intake data set 110 (and assuming that the new value is valid), the new value will be placed in the appropriate group as defined by a (human) dietary intake scientist. If the new item is for a food not previously tracked, then a (human) dietary intake scientist will define a new food recipe in file 145 based on the nutrition data set 120 and the values of the eight dimension fields within the new foods data file 144, and insert this new item into the food-portion link file 150 so that later encounters with this same food item can be used to obtain corresponding nutrition information (FIG. 8A, blocks 1154, 1152). As shown in FIG. 8A, the exception handling that can be performed after the data reduction algorithm 500 has completed based on the new foods file 1144 contents. If, after the data reduction algorithm 500, there are new foods defined within the new foods file 1144 ("yes" exit to decision block 1150), then for each new food identified, a dietician creates a new recipe (or updates an existing one) from the dietary intake data set 110, assigns an associated portion code, and adds this new (or updated) record to the food-portion links table 150 (block 1152). The data reduction algorithm 500 is preferably run again until no more exceptions are generated—meaning that all foods defined within diary 1126 have been defined. At this point ("no" exit to decision block 1150), the preferred exemplary routine 1100 exports two deliverables (the diary file 1126 concatenated with the nutrition data set 120, and the master household file 160) in the form of an output data set 140 for final processing (block 1156).

Figure 8E:
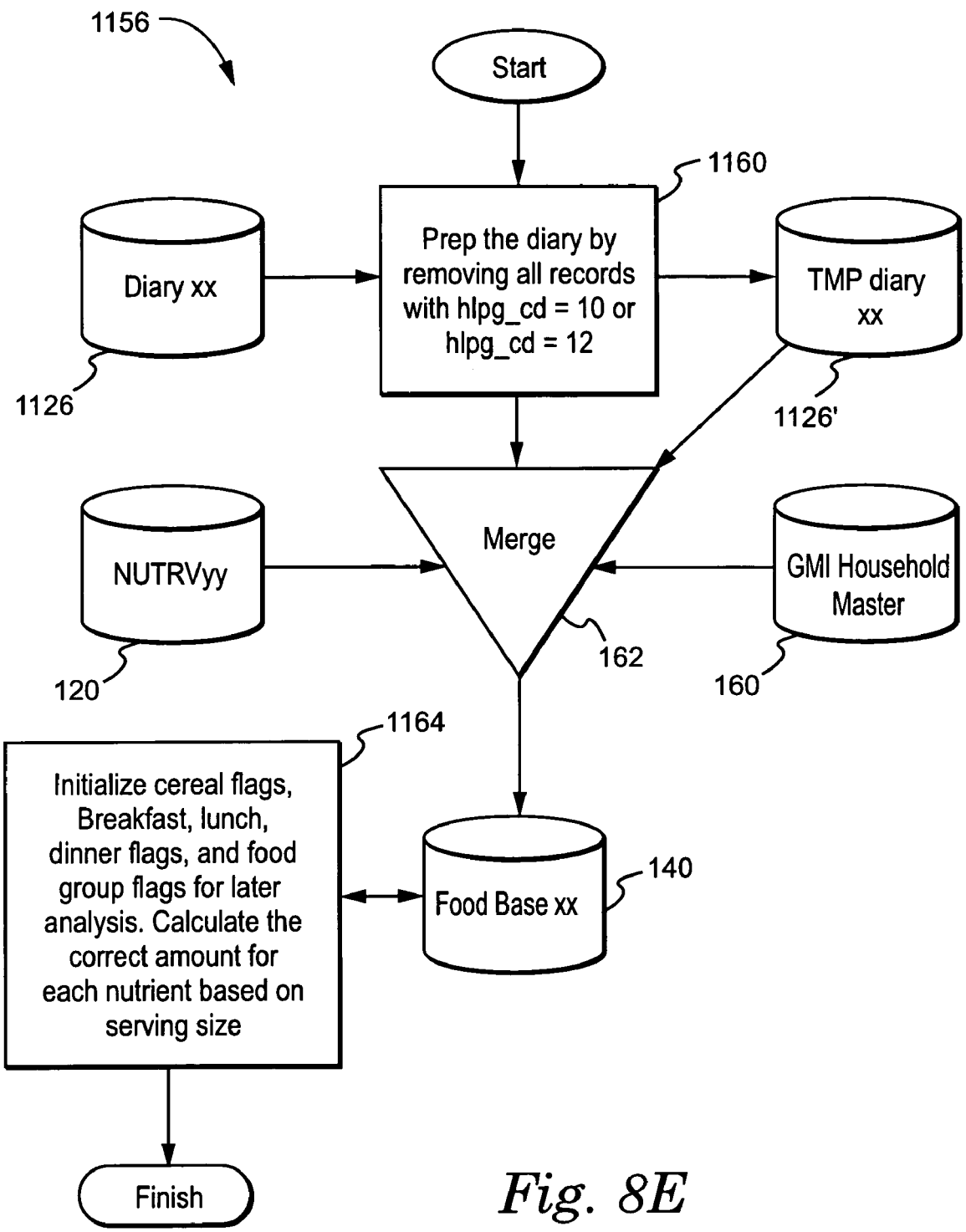

FIG. 8E shows an example illustrative flowchart for the final merge routine 1156 shown in FIG. 8A. In the FIG. 8E example, the diary file 1126 is prepared by removing all records indicating non-reported meals as described above (block 1160), to result in a temporary diary file 1126'. This temporary diary file 1126' is merged with the nutrient data set 120 (or at least applicable portions thereof) and the household master file 160 (merge block 1162) to generate a food base output data set 140. In the specific example embodiment described here for non-limiting but illustrative purposes, the routine 1156 proceeds to initialize cereal flags, breakfast and lunch and dinner flags, and food group flags for later analysis and calculates the correct amount of each nutrient based on serving size (block 1164).

The following is one example excerpt from the exemplary output file 140 corresponding to one day of one person's data. This output file 140 represents the final combination of the portion size information from the portion size data set 130 (fields portion_cd, srvng_sz), all nutrients from the nutrient data set 120 (calculated based on serving size (nutrient_cd, energy-tot_sugar), and additional defined fields (e.g., cereal_ind, whl_grn_ind, etc.). This is the output file that the exemplary embodiment generates from the SAS® program genBIHNStudy shown in block 1030 and described in the flowcharts of FIGS. 8A–8E.

| person | GMI MEAL SMRY | HSHLD ID | DAY NBR | HLP G CD | YEAR | FOOD CD | FOOD NM | FOOD GRP MIN | FOOD GRP MJR CD |
|---|---|---|---|---|---|---|---|---|---|
| 108538 | 1 | 49805 | 2 | 1 | 19 | 111106 | Oats, Instant, Plain, NSF | 78 | 1900 |
| 108538 | 1 | 49805 | 2 | 1 | 19 | 11001 | Regular, Caffeinated, NSF | 118 | 1100 |
| 108538 | 1 | 49805 | 2 | 1 | 19 | 31867 | Skim milk | 24C | 2200 |
| 108538 | 1 | 49805 | 2 | 1 | 19 | 41375 | Tomato Juice | 62 | 1800 |
| 108538 | 1 | 49805 | 2 | 1 | 19 | 101136 | Raisin Bran | 77C | 1900 |
| 108538 | 1 | 49805 | 2 | 1 | 19 | 5012361 | Bagels, Regular White or NR, Untoasted | 74 | 1900 |
| 108538 | 2 | 49805 | 2 | 1 | 19 | 271154 | Regular Sugar Hyd Banana or NR, Fresh, Reg Sugar | 63A | 1800 |
| 108538 | 2 | 49805 | 2 | 1 | 19 | 441882 | Peanut Butter, Reduced Fat | 60B | 1700 |
| 108538 | 2 | 49805 | 2 | 1 | 19 | 5213731 | Cracker, Regular Butter, Regular | 90 | 2300 |
| 108538 | 3 | 49805 | 2 | 1 | 19 | 253275 | Vegetable, Plain, Black Beans, Cooked | 70 | 2600 |
| 108538 | 3 | 49805 | 2 | 1 | 19 | 253931 | Combination Vegetable Dish, Plain Mixed Veg, Ckd | 69 | 2600 |
| 108538 | 3 | 49805 | 2 | 1 | 19 | 253310 | Vegetable. Plain, Beets, Raw | 68 | 2600 |
| 108538 | 3 | 49805 | 2 | 1 | 19 | 412062 | Ketchup, Regular | 125 | 2300 |
| 108538 | 3 | 49805 | 2 | 1 | 19 | 331864 | Apple Pie | 102 | 1500 |
| 108538 | 3 | 49805 | 2 | 1 | 19 | 5013062 | Buns/Rolls, Regular Corn, Toasted | 75A | 1900 |
| 108538 | 3 | 49805 | 2 | 1 | 19 | 284168 | Ice Cream, Diet/Lowcal/Sorbet, Van or NR, Reg Fa | 27 | 2200 |
| 108538 | 4 | 49805 | 2 | 1 | 19 | 387384 | popcorn light | 84 | 2300 |

| Person | Gmi Meal Smry | Portion Cd | Srvng Sz | Cereal Ind | Whl Grn Ind | Nutrient Cd | Consumed | Skipped | Breakfast | Lunch | Dinner | Snack |
|---|---|---|---|---|---|---|---|---|---|---|---|---|
| 108538 | 1 | 5678 | 234.62 | 0 | 1 | 110001 | 1 | 0 | 1 | 0 | 0 | 0 |
| 108538 | 1 | 9133 | 346.33 | 0 | 0 | 10017 | 1 | 0 | 1 | 0 | 0 | 0 |
| 108538 | 1 | 1013 | 96.25 | 0 | 0 | 30002 | 1 | 0 | 1 | 0 | 0 | 0 |
| 108538 | 1 | 9386 | 209.81 | 0 | 0 | 40016 | 1 | 0 | 1 | 0 | 0 | 0 |
| 108538 | 1 | 5804 | 54.84 | 1 | 0 | 100058 | 1 | 0 | 1 | 0 | 0 | 0 |
| 108538 | 1 | 5110 | 56.09 | 0 | 0 | 500113 | 1 | 0 | 1 | 0 | 0 | 0 |
| 108538 | 2 | 6004 | 88.12 | 0 | 0 | 270021 | 1 | 0 | 0 | 1 | 0 | 0 |
| 108538 | 2 | 4100 | 28.04 | 0 | 0 | 440003 | 1 | 0 | 0 | 1 | 0 | 0 |
| 108538 | 2 | 5478 | 14.29 | 0 | 0 | 520003 | 1 | 0 | 0 | 1 | 0 | 0 |
| 108538 | 3 | 7379 | 104.66 | 0 | 0 | 250006 | 1 | 0 | 0 | 0 | 1 | 0 |
| 108538 | 3 | 7268 | 124.34 | 0 | 0 | 250156 | 1 | 0 | 0 | 0 | 1 | 0 |
| 108538 | 3 | 7296 | 51.17 | 0 | 0 | 250036 | 1 | 0 | 0 | 0 | 1 | 0 |
| 108538 | 3 | 7132 | 12.8 | 0 | 0 | 410040 | 1 | 0 | 0 | 0 | 1 | 0 |
| 108538 | 3 | 5350 | 175.8 | 0 | 0 | 330003 | 1 | 0 | 0 | 0 | 1 | 0 |
| 108538 | 3 | 5148 | 63.2 | 0 | 0 | 500095 | 1 | 0 | 0 | 0 | 1 | 0 |
| 108538 | 3 | 1179 | 99.99 | 0 | 0 | 280013 | 1 | 0 | 0 | 0 | 1 | 0 |
| 108538 | 4 | 5530 | 87 | 0 | 0 | 380040 | 1 | 0 | 0 | 0 | 0 | 1 |

| Person | Gmi Meal Smry | Cereal | Whl Grm | Yogurt | Rte | Coffee | Tea | Presweet | Energy | Tot Fat | Tot Carb | Tot Protein |
|---|---|---|---|---|---|---|---|---|---|---|---|---|
| 108538 | 1 | 0 | 1 | 0 | 0 | 0 | 0 | 0 | 138.43 | 2.30 | 24.00 | 5.82 |
| 108538 | 1 | 0 | 0 | 0 | 0 | 1 | 0 | 0 | 6.93 | 0.00 | 1.39 | 0.35 |
| 108538 | 1 | 0 | 0 | 0 | 0 | 0 | 0 | 0 | 33.60 | 0.17 | 4.67 | 3.28 |
| 108538 | 1 | 0 | 0 | 0 | 0 | 0 | 0 | 0 | 35.67 | 0.13 | 8.87 | 1.59 |
| 108538 | 1 | 1 | 0 | 0 | 1 | 0 | 0 | 0 | 167.26 | 1.32 | 42.34 | 5.05 |
| 108538 | 1 | 0 | 0 | 0 | 0 | 0 | 0 | 0 | 154.25 | 0.90 | 29.95 | 5.89 |
| 108538 | 2 | 0 | 0 | 0 | 0 | 0 | 0 | 0 | 81.07 | 0.42 | 20.65 | 0.91 |
| 108538 | 2 | 0 | 0 | 0 | 0 | 0 | 0 | 0 | 145.86 | 9.35 | 10.13 | 7.01 |

-continued

| Person | Gmi Meal Smry | Cereal | Whl Grm | Yogurt | Rte | Coffee | Tea | Presweet | Energy | Tot Fat | Tot Carb | Tot Protein |
|---|---|---|---|---|---|---|---|---|---|---|---|---|
| 108538 | 2 | 0 | 0 | 0 | 0 | 0 | 0 | 0 | 72.62 | 4.02 | 8.07 | 1.00 |
| 108538 | 3 | 0 | 0 | 0 | 0 | 0 | 0 | 0 | 148.47 | 0.60 | 27.50 | 9.09 |
| 108538 | 3 | 0 | 0 | 0 | 0 | 0 | 0 | 0 | 31.87 | 0.21 | 6.39 | 2.79 |
| 108538 | 3 | 0 | 0 | 0 | 0 | 0 | 0 | 0 | 21.61 | 0.09 | 4.89 | 0.82 |
| 108538 | 3 | 0 | 0 | 0 | 0 | 0 | 0 | 0 | 13.31 | 0.05 | 3.49 | 0.19 |
| 108538 | 3 | 0 | 0 | 0 | 0 | 0 | 0 | 0 | 421.92 | 20.11 | 58.15 | 3.74 |
| 108538 | 3 | 0 | 0 | 0 | 0 | 0 | 0 | 0 | 212.36 | 7.76 | 31.25 | 4.20 |
| 108538 | 3 | 0 | 0 | 0 | 0 | 0 | 0 | 0 | 97.17 | 0.09 | 24.84 | 0.40 |
| 108538 | 4 | 0 | 0 | 0 | 0 | 0 | 0 | 0 | 384.35 | 15.23 | 56.42 | 8.69 |

| Person | Gmi Meal Smry | Anml Protein | Veg Protein | Alcohol | Cholest | Tot Sat Fat Acid | Tot Musat Fat Acid | Tot Pusat Fat Acid | Fructose | Galactose | Glucose | Lactose |
|---|---|---|---|---|---|---|---|---|---|---|---|---|
| 108538 | 1 | 0.00 | 5.82 | 0.00 | 0.00 | 0.40 | 0.73 | 0.84 | 0.05 | 0.00 | 0.00 | 0.00 |
| 108538 | 1 | 0.00 | 0.00 | 0.00 | 0.00 | 0.00 | 0.00 | 0.00 | 0.00 | 0.00 | 0.00 | 0.00 |
| 108538 | 1 | 3.27 | 0.00 | 0.00 | 1.73 | 0.12 | 0.05 | 0.01 | 0.00 | 0.00 | 0.00 | 4.24 |
| 108538 | 1 | 0.00 | 0.00 | 0.00 | 0.00 | 0.02 | 0.02 | 0.04 | 3.99 | 0.00 | 2.94 | 0.00 |
| 108538 | 1 | 0.00 | 5.05 | 0.00 | 0.00 | 0.13 | 0.22 | 0.71 | 2.96 | 0.00 | 3.45 | 0.00 |
| 108538 | 1 | 0.00 | 5.89 | 0.00 | 0.00 | 0.12 | 0.07 | 0.39 | 0.11 | 0.00 | 0.22 | 0.00 |
| 108538 | 2 | 0.00 | 0.88 | 0.00 | 0.00 | 0.16 | 0.04 | 0.08 | 2.38 | 0.00 | 3.70 | 0.00 |
| 108538 | 2 | 0.00 | 7.01 | 0.00 | 0.00 | 1.47 | 4.28 | 3.03 | 0.00 | 0.00 | 0.06 | 0.00 |
| 108538 | 2 | 0.00 | 1.00 | 0.00 | 0.00 | 0.99 | 2.30 | 0.53 | 0.03 | 0.00 | 0.06 | 0.00 |
| 108538 | 3 | 0.00 | 9.09 | 0.00 | 0.00 | 0.16 | 0.05 | 0.26 | 0.84 | 0.00 | 0.63 | 0.00 |
| 108538 | 3 | 0.00 | 2.79 | 0.00 | 0.00 | 0.02 | 0.01 | 0.11 | 0.56 | 0.00 | 0.62 | 0.00 |
| 108538 | 3 | 0.00 | 0.82 | 0.00 | 0.00 | 0.02 | 0.02 | 0.03 | 0.05 | 0.00 | 0.10 | 0.00 |
| 108538 | 3 | 0.00 | 0.19 | 0.00 | 0.00 | 0.01 | 0.01 | 0.02 | 0.46 | 0.00 | 0.96 | 0.00 |
| 108538 | 3 | 0.00 | 3.78 | 0.00 | 0.00 | 5.03 | 8.79 | 5.29 | 6.84 | 0.00 | 2.41 | 0.00 |
| 108538 | 3 | 1.52 | 2.67 | 0.00 | 31.25 | 3.36 | 2.88 | 0.81 | 0.16 | 0.00 | 0.37 | 1.08 |
| 108538 | 3 | 0.00 | 0.40 | 0.00 | 0.00 | 0.00 | 0.01 | 0.05 | 0.56 | 0.00 | 0.62 | 0.00 |
| 108538 | 4 | 0.00 | 8.69 | 0.00 | 0.00 | 3.17 | 8.14 | 2.76 | 0.07 | 0.00 | 0.07 | 0.00 |

| Vperson | Gmi Meal Smry | Maltose | Sucrose | Starch | Tot Diet Fib | Sol Diet Fib | Insol Diet Fib | Pectins | Tot Vitm A | Bc Equiv | Retinol | Vitm D |
|---|---|---|---|---|---|---|---|---|---|---|---|---|
| 108538 | 1 | 0.00 | 0.52 | 21.02 | 4.08 | 1.90 | 2.21 | 0.00 | 853.87 | 0.00 | 601.61 | 0.00 |
| 108538 | 1 | 0.00 | 0.00 | 0.10 | 0.38 | 0.21 | 0.21 | 0.00 | 0.00 | 0.00 | 0.00 | 0.00 |
| 108538 | 1 | 0.00 | 0.00 | 0.00 | 0.00 | 0.00 | 0.00 | 0.00 | 204.00 | 1.93 | 57.75 | 0.98 |
| 108538 | 1 | 0.00 | 0.00 | 0.00 | 0.84 | 0.46 | 0.38 | 0.46 | 556.00 | 698.52 | 0.00 | 0.00 |
| 108538 | 1 | 0.90 | 8.54 | 18.52 | 7.35 | 0.92 | 6.43 | 0.11 | 1364.00 | 0.40 | 224.43 | 1.24 |
| 108538 | 1 | 0.00 | 0.15 | 25.73 | 1.29 | 0.50 | 0.79 | 0.00 | 0.00 | 0.00 | 0.00 | 0.00 |
| 108538 | 2 | 0.00 | 5.73 | 3.52 | 2.11 | 0.53 | 1.59 | 0.53 | 81.00 | 43.18 | 0.00 | 0.00 |
| 108538 | 2 | 0.19 | 2.34 | 6.40 | 0.68 | 0.20 | 0.48 | 0.22 | 0.00 | 0.00 | 0.00 | 0.00 |
| 108538 | 2 | 0.00 | 0.75 | 6.75 | 0.26 | 0.15 | 0.11 | 0.00 | 0.00 | 0.00 | 0.00 | 0.00 |
| 108538 | 3 | 0.00 | 1.57 | 9.72 | 6.69 | 2.51 | 4.19 | 0.00 | 2.00 | 1.26 | 0.00 | 0.00 |
| 108538 | 3 | 0.00 | 0.65 | 0.82 | 3.61 | 1.41 | 2.20 | 0.91 | 3209.73 | 2389.84 | 0.00 | 0.00 |
| 108538 | 3 | 0.00 | 4.18 | 0.34 | 0.98 | 0.59 | 0.39 | 0.22 | 33.60 | 10.30 | 0.00 | 0.00 |
| 108538 | 3 | 0.35 | 1.42 | 0.00 | 0.17 | 0.04 | 0.13 | 0.00 | 1016.00 | 77.87 | 0.00 | 0.00 |
| 108538 | 3 | 0.00 | 19.29 | 23.91 | 2.50 | 1.00 | 1.37 | 0.37 | 20.47 | 21.11 | 0.00 | 0.00 |
| 108538 | 3 | 0.08 | 8.78 | 19.90 | 1.36 | 0.25 | 1.11 | 0.00 | 211.03 | 42.02 | 18.97 | 0.31 |
| 108538 | 3 | 0.00 | 21.18 | 0.00 | 2.51 | 0.28 | 2.23 | 0.28 | 34.20 | 20.52 | 0.00 | 0.00 |
| 108538 | 4 | 0.00 | 0.29 | 38.82 | 10.94 | 0.37 | 10.57 | 0.00 | 163.17 | 85.01 | 0.00 | 0.00 |

| Person | Gmi Meal Smry | Vitm D | Tot Vitm E | Alpha Toc | Beta Toc | Gamma Toc | Delta Toc | Vitm K | Vitm C | Thiamin | Riboflavin | Niacin |
|---|---|---|---|---|---|---|---|---|---|---|---|---|
| 108538 | 1 | 0.00 | 0.26 | 0.16 | 0.12 | 0.35 | 0.00 | 1.13 | 0.00 | 0.70 | 0.38 | 7.27 |
| 108538 | 1 | 0.00 | 0.00 | 0.00 | 0.00 | 0.00 | 0.00 | 0.07 | 0.00 | 0.00 | 0.00 | 0.76 |
| 108538 | 1 | 0.98 | 0.04 | 0.04 | 0.00 | 0.00 | 0.00 | 0.01 | 0.94 | 0.04 | 0.13 | 0.09 |
| 108538 | 1 | 0.00 | 1.91 | 1.91 | 0.00 | 0.00 | 0.00 | 4.83 | 38.40 | 0.10 | 0.06 | 1.41 |

-continued

| Person | Gmi Meal Smry | Vitm D | Tot Vitm E | Alpha Toc | Beta Toc | Gamma Toc | Delta Toc | Vitm K | Vitm C | Thiamin | Riboflavin | Niacin |
|---|---|---|---|---|---|---|---|---|---|---|---|---|
| 108538 | 1 | 1.24 | 0.50 | 0.40 | 0.25 | 0.00 | 0.00 | 0.88 | 0.00 | 0.38 | 0.44 | 4.99 |
| 108538 | 1 | 0.00 | 0.02 | 0.02 | 0.00 | 0.00 | 0.00 | 0.22 | 0.00 | 0.30 | 0.18 | 2.56 |
| 108538 | 2 | 0.00 | 0.24 | 0.24 | 0.00 | 0.00 | 0.00 | 0.18 | 8.02 | 0.04 | 0.09 | 0.48 |
| 108538 | 2 | 0.00 | 1.42 | 1.21 | 0.05 | 1.62 | 0.17 | 1.69 | 0.00 | 0.03 | 0.02 | 1.27 |
| 108538 | 2 | 0.00 | 0.59 | 0.32 | 0.00 | 2.60 | 1.07 | 7.64 | 0.00 | 0.08 | 0.05 | 0.57 |
| 108538 | 3 | 0.00 | 0.19 | 0.15 | 0.00 | 0.42 | 0.42 | 0.88 | 0.94 | 0.21 | 0.06 | 0.55 |
| 108538 | 3 | 0.00 | 1.01 | 0.98 | 0.00 | 0.14 | 0.00 | 76.85 | 40.58 | 0.06 | 0.09 | 0.50 |
| 108538 | 3 | 0.00 | 0.15 | 0.12 | 0.06 | 0.06 | 0.00 | 0.59 | 1.77 | 0.02 | 0.02 | 0.16 |
| 108538 | 3 | 0.00 | 0.19 | 0.19 | 0.00 | 0.00 | 0.00 | 0.46 | 1.93 | 0.01 | 0.01 | 0.18 |
| 108538 | 3 | 0.00 | 1.67 | 0.69 | 0.02 | 9.46 | 2.67 | 19.92 | 1.51 | 0.28 | 0.19 | 2.25 |
| 108538 | 3 | 0.31 | 0.48 | 0.37 | 0.01 | 1.04 | 0.00 | 0.40 | 0.21 | 0.23 | 0.20 | 1.57 |
| 108538 | 3 | 0.00 | 0.26 | 0.15 | 0.00 | 0.86 | 1.54 | 0.49 | 9.41 | 0.01 | 0.03 | 0.13 |
| 108538 | 4 | 0.00 | 1.87 | 0.95 | 0.19 | 8.38 | 0.39 | 9.40 | 0.00 | 0.15 | 0.20 | 1.41 |

| Person | Gmi Meal Smry | Pn Acid | Vitm B6 | Folate | Vitm B12 | Calcium | Phosphorus | Magnesium | Iron | Zinc | Copper | Selenium |
|---|---|---|---|---|---|---|---|---|---|---|---|---|
| 108538 | 1 | 0.47 | 0.99 | 199.22 | 0.00 | 219.96 | 175.57 | 56.43 | 8.35 | 1.15 | 0.12 | 12.76 |
| 108538 | 1 | 0.00 | 0.00 | 0.35 | 0.00 | 6.93 | 3.46 | 17.32 | 0.17 | 0.07 | 0.03 | 0.35 |
| 108538 | 1 | 0.32 | 0.04 | 5.01 | 0.37 | 118.77 | 97.12 | 10.93 | 0.04 | 0.39 | 0.01 | 2.02 |
| 108538 | 1 | 0.52 | 0.23 | 41.75 | 0.00 | 18.88 | 39.86 | 23.08 | 1.22 | 0.29 | 0.21 | 1.05 |
| 108538 | 1 | 0.36 | 0.49 | 109.68 | 1.48 | 31.81 | 192.49 | 80.07 | 4.50 | 3.73 | 0.22 | 24.35 |
| 108538 | 1 | 0.20 | 0.03 | 12.34 | 0.00 | 41.51 | 53.85 | 16.27 | 2.00 | 0.49 | 0.09 | 17.95 |
| 108538 | 2 | 0.23 | 0.51 | 16.83 | 0.00 | 5.29 | 17.62 | 25.55 | 0.27 | 0.14 | 0.09 | 0.97 |
| 108538 | 2 | 0.12 | 0.03 | 20.34 | 0.00 | 17.16 | 85.49 | 17.60 | 0.94 | 0.79 | 0.19 | 1.71 |
| 108538 | 2 | 0.04 | 0.00 | 2.51 | 0.00 | 1.53 | 10.43 | 2.12 | 0.45 | 0.07 | 0.01 | 3.29 |
| 108538 | 3 | 0.27 | 0.17 | 146.27 | 0.00 | 73.44 | 164.15 | 61.70 | 2.60 | 1.11 | 0.31 | 6.10 |
| 108538 | 3 | 0.25 | 0.15 | 56.64 | 0.00 | 42.36 | 48.16 | 17.92 | 0.66 | 0.29 | 0.05 | 1.67 |
| 108538 | 3 | 0.07 | 0.04 | 39.30 | 0.00 | 7.86 | 18.67 | 11.30 | 0.39 | 0.17 | 0.04 | 0.44 |
| 108538 | 3 | 0.02 | 0.02 | 1.92 | 0.00 | 2.43 | 4.99 | 2.82 | 0.09 | 0.03 | 0.03 | 0.10 |
| 108538 | 3 | 0.28 | 0.05 | 9.74 | 0.00 | 11.27 | 46.11 | 11.55 | 1.79 | 0.28 | 0.09 | 12.08 |
| 108538 | 3 | 0.27 | 0.06 | 13.99 | 0.15 | 100.36 | 84.37 | 12.50 | 1.46 | 0.35 | 0.04 | 8.70 |
| 108538 | 3 | 0.09 | 0.02 | 14.82 | 0.00 | 9.24 | 9.89 | 7.55 | 0.38 | 0.11 | 0.05 | 0.18 |
| 108538 | 4 | 0.31 | 0.17 | 16.66 | 0.00 | 7.82 | 217.28 | 94.91 | 1.93 | 2.50 | 0.30 | 5.39 |

| Person | Gmi Meal Smry | Sodium | Potassium | Butyric Acid | Caproic Acid | Caprylic Acid | Capric Acid | Lauric Acid | Myristic Acid | Palmitic Acid | Margaric Acid | Stearic Acid |
|---|---|---|---|---|---|---|---|---|---|---|---|---|
| 108538 | 1 | 380.08 | 132.79 | 0.00 | 0.00 | 0.00 | 0.00 | 0.00 | 0.00 | 0.35 | 0.00 | 0.02 |
| 108538 | 1 | 6.93 | 187.02 | 0.00 | 0.00 | 0.00 | 0.00 | 0.00 | 0.00 | 0.00 | 0.00 | 0.00 |
| 108538 | 1 | 49.57 | 159.39 | 0.01 | 0.00 | 0.00 | 0.00 | 0.00 | 0.02 | 0.05 | 0.00 | 0.02 |
| 108538 | 1 | 757.41 | 461.58 | 0.00 | 0.00 | 0.00 | 0.00 | 0.00 | 0.00 | 0.02 | 0.00 | 0.00 |
| 108538 | 1 | 318.07 | 392.65 | 0.00 | 0.00 | 0.00 | 0.00 | 0.00 | 0.00 | 0.12 | 0.00 | 0.01 |
| 108538 | 1 | 299.52 | 56.65 | 0.00 | 0.00 | 0.00 | 0.00 | 0.00 | 0.00 | 0.12 | 0.00 | 0.01 |
| 108538 | 2 | 0.88 | 348.96 | 0.00 | 0.00 | 0.00 | 0.00 | 0.00 | 0.00 | 0.11 | 0.00 | 0.01 |
| 108538 | 2 | 157.21 | 143.63 | 0.00 | 0.00 | 0.00 | 0.00 | 0.00 | 0.00 | 0.99 | 0.00 | 0.23 |
| 108538 | 2 | 120.94 | 10.36 | 0.00 | 0.00 | 0.00 | 0.00 | 0.00 | 0.00 | 0.46 | 0.00 | 0.53 |
| 108538 | 3 | 402.23 | 384.85 | 0.00 | 0.00 | 0.00 | 0.00 | 0.00 | 0.00 | 0.15 | 0.00 | 0.01 |
| 108538 | 3 | 506.93 | 207.10 | 0.00 | 0.00 | 0.00 | 0.00 | 0.00 | 0.00 | 0.02 | 0.00 | 0.00 |
| 108538 | 3 | 37.82 | 149.83 | 0.00 | 0.00 | 0.00 | 0.00 | 0.00 | 0.00 | 0.02 | 0.00 | 0.00 |
| 108538 | 3 | 151.81 | 61.57 | 0.00 | 0.00 | 0.00 | 0.00 | 0.00 | 0.00 | 0.01 | 0.00 | 0.00 |
| 108538 | 3 | 289.09 | 129.86 | 0.00 | 0.00 | 0.00 | 0.00 | 0.00 | 0.11 | 2.85 | 0.00 | 2.09 |
| 108538 | 3 | 510.37 | 80.17 | 0.01 | 0.01 | 0.01 | 0.01 | 0.01 | 0.26 | 1.85 | 0.00 | 1.18 |
| 108538 | 3 | 0.86 | 65.17 | 0.00 | 0.00 | 0.00 | 0.00 | 0.00 | 0.00 | 0.00 | 0.00 | 0.00 |
| 108538 | 4 | 930.19 | 218.20 | 0.00 | 0.00 | 0.00 | 0.00 | 0.00 | 0.00 | 1.74 | 0.00 | 1.31 |

| Person | Gmi Meal Smry | Arachidic Acid | Behenic Acid | Myristoleic Acid | Palmitoleic Acid | Oleic Acid | Gadoleic Acid | Erucic Acid | Linoleic Acid | Linolenic Acid | Parinaric Acid | Arachidonic Acid |
|---|---|---|---|---|---|---|---|---|---|---|---|---|
| 108538 | 1 | 0.00 | 0.00 | 0.00 | 0.00 | 0.73 | 0.00 | 0.00 | 0.80 | 0.05 | 0.00 | 0.00 |
| 108538 | 1 | 0.00 | 0.00 | 0.00 | 0.00 | 0.00 | 0.00 | 0.00 | 0.00 | 0.00 | 0.00 | 0.00 |

-continued

| Person | Gmi Meal Smry | Arachidic Acid | Behenic Acid | Myristoleic Acid | Palmitoleic Acid | Oleic Acid | Gadoleic Acid | Erucic Acid | Linoleic Acid | Linolenic Acid | Parinaric Acid | Arachidonic Acid |
|---|---|---|---|---|---|---|---|---|---|---|---|---|
| 108538 | 1 | 0.00 | 0.00 | 0.00 | 0.01 | 0.04 | 0.00 | 0.00 | 0.00 | 0.00 | 0.00 | 0.00 |
| 108538 | 1 | 0.00 | 0.00 | 0.00 | 0.00 | 0.02 | 0.00 | 0.00 | 0.04 | 0.00 | 0.00 | 0.00 |
| 108538 | 1 | 0.00 | 0.00 | 0.00 | 0.00 | 0.09 | 0.00 | 0.00 | 0.32 | 0.03 | 0.00 | 0.00 |
| 108538 | 1 | 0.00 | 0.00 | 0.00 | 0.01 | 0.07 | 0.00 | 0.00 | 0.37 | 0.02 | 0.00 | 0.00 |
| 108538 | 2 | 0.00 | 0.00 | 0.00 | 0.01 | 0.03 | 0.00 | 0.00 | 0.05 | 0.03 | 0.00 | 0.00 |
| 108538 | 2 | 0.05 | 0.10 | 0.00 | 0.00 | 4.16 | 0.11 | 0.00 | 2.97 | 0.06 | 0.00 | 0.00 |
| 108538 | 2 | 0.00 | 0.00 | 0.00 | 0.00 | 2.30 | 0.00 | 0.00 | 0.53 | 0.00 | 0.00 | 0.00 |
| 108538 | 3 | 0.00 | 0.00 | 0.00 | 0.00 | 0.05 | 0.00 | 0.00 | 0.14 | 0.12 | 0.00 | 0.00 |
| 108538 | 3 | 0.00 | 0.00 | 0.00 | 0.00 | 0.01 | 0.00 | 0.00 | 0.02 | 0.07 | 0.00 | 0.00 |
| 108538 | 3 | 0.00 | 0.00 | 0.00 | 0.00 | 0.02 | 0.00 | 0.00 | 0.03 | 0.00 | 0.00 | 0.00 |
| 108538 | 3 | 0.00 | 0.00 | 0.00 | 0.00 | 0.01 | 0.00 | 0.00 | 0.02 | 0.00 | 0.00 | 0.00 |
| 108538 | 3 | 0.00 | 0.00 | 0.00 | 0.00 | 8.79 | 0.00 | 0.00 | 4.96 | 0.32 | 0.00 | 0.00 |
| 108538 | 3 | 0.00 | 0.00 | 0.00 | 0.30 | 2.57 | 0.00 | 0.00 | 0.75 | 0.04 | 0.00 | 0.01 |
| 108538 | 3 | 0.00 | 0.00 | 0.00 | 0.00 | 0.01 | 0.00 | 0.00 | 0.04 | 0.02 | 0.00 | 0.00 |
| 108538 | 4 | 0.04 | 0.00 | 0.00 | 0.06 | 8.06 | 0.02 | 0.00 | 2.69 | 0.08 | 0.00 | 0.00 |

| Person | Gmi Meal Smry | Eicos Acid | Docosp Enoic Acid | Docosh Enoic Acid | Tryptophan | Threonine | Isoleucine | Leucine | Lysine | Methionine | Cystine | Phenylalanine |
|---|---|---|---|---|---|---|---|---|---|---|---|---|
| 108538 | 1 | 0.00 | 0.00 | 0.00 | 0.07 | 0.19 | 0.23 | 0.45 | 0.23 | 0.12 | 0.14 | 0.31 |
| 108538 | 1 | 0.00 | 0.00 | 0.00 | 0.00 | 0.00 | 0.00 | 0.03 | 0.00 | 0.00 | 0.00 | 0.00 |
| 108538 | 1 | 0.00 | 0.00 | 0.00 | 0.05 | 0.14 | 0.20 | 0.32 | 0.26 | 0.09 | 0.03 | 0.15 |
| 108538 | 1 | 0.00 | 0.00 | 0.00 | 0.00 | 0.04 | 0.04 | 0.04 | 0.04 | 0.00 | 0.00 | 0.04 |
| 108538 | 1 | 0.00 | 0.00 | 0.00 | 0.08 | 0.15 | 0.18 | 0.32 | 0.15 | 0.07 | 0.11 | 0.22 |
| 108538 | 1 | 0.00 | 0.00 | 0.00 | 0.07 | 0.17 | 0.22 | 0.42 | 0.14 | 0.11 | 0.12 | 0.29 |
| 108538 | 2 | 0.00 | 0.00 | 0.00 | 0.01 | 0.03 | 0.03 | 0.06 | 0.04 | 0.01 | 0.02 | 0.04 |
| 108538 | 2 | 0.00 | 0.00 | 0.00 | 0.09 | 0.25 | 0.31 | 0.51 | 0.37 | 0.09 | 0.09 | 0.37 |
| 108538 | 2 | 0.00 | 0.00 | 0.00 | 0.01 | 0.03 | 0.03 | 0.07 | 0.02 | 0.02 | 0.02 | 0.05 |
| 108538 | 3 | 0.00 | 0.00 | 0.00 | 0.10 | 0.39 | 0.40 | 0.73 | 0.63 | 0.14 | 0.10 | 0.49 |
| 108538 | 3 | 0.00 | 0.00 | 0.00 | 0.02 | 0.10 | 0.10 | 0.12 | 0.14 | 0.04 | 0.02 | 0.09 |
| 108538 | 3 | 0.00 | 0.00 | 0.00 | 0.01 | 0.03 | 0.03 | 0.04 | 0.03 | 0.01 | 0.01 | 0.03 |
| 108538 | 3 | 0.00 | 0.00 | 0.00 | 0.00 | 0.01 | 0.00 | 0.01 | 0.01 | 0.00 | 0.00 | 0.00 |
| 108538 | 3 | 0.00 | 0.00 | 0.00 | 0.05 | 0.11 | 0.14 | 0.25 | 0.09 | 0.05 | 0.07 | 0.18 |
| 108538 | 3 | 0.00 | 0.00 | 0.00 | 0.05 | 0.15 | 0.18 | 0.39 | 0.18 | 0.09 | 0.08 | 0.21 |
| 108538 | 3 | 0.00 | 0.00 | 0.00 | 0.00 | 0.00 | 0.00 | 0.00 | 0.00 | 0.00 | 0.00 | 0.00 |
| 108538 | 4 | 0.00 | 0.00 | 0.00 | 0.06 | 0.32 | 0.31 | 1.06 | 0.24 | 0.18 | 0.16 | 0.43 |

| Person | Gmi Meal Smry | Tyrosine | Valine | Arginine | Histidine | Alanine | Aspartic Acid | Glutamic | Glycine | Proline | Serine | Aspartame |
|---|---|---|---|---|---|---|---|---|---|---|---|---|
| 108538 | 1 | 0.19 | 0.33 | 0.40 | 0.14 | 0.31 | 0.49 | 1.27 | 0.28 | 0.33 | 0.26 | 0.00 |
| 108538 | 1 | 0.00 | 0.00 | 0.00 | 0.00 | 0.00 | 0.03 | 0.07 | 0.00 | 0.00 | 0.00 | 0.00 |
| 108538 | 1 | 0.15 | 0.22 | 0.12 | 0.09 | 0.12 | 0.25 | 0.68 | 0.07 | 0.32 | 0.17 | 0.00 |
| 108538 | 1 | 0.02 | 0.04 | 0.04 | 0.02 | 0.04 | 0.21 | 0.63 | 0.02 | 0.04 | 0.04 | 0.00 |
| 108538 | 1 | 0.14 | 0.23 | 0.30 | 0.13 | 0.20 | 0.28 | 1.39 | 0.22 | 0.48 | 0.24 | 0.00 |
| 108538 | 1 | 0.17 | 0.26 | 0.21 | 0.13 | 0.20 | 0.27 | 1.96 | 0.21 | 0.66 | 0.29 | 0.00 |
| 108538 | 2 | 0.02 | 0.04 | 0.04 | 0.07 | 0.04 | 0.10 | 0.10 | 0.04 | 0.04 | 0.04 | 0.00 |
| 108538 | 2 | 0.26 | 0.32 | 0.63 | 0.18 | 0.28 | 0.82 | 1.41 | 0.33 | 0.37 | 0.36 | 0.00 |
| 108538 | 2 | 0.03 | 0.04 | 0.04 | 0.02 | 0.03 | 0.04 | 0.34 | 0.04 | 0.12 | 0.05 | 0.00 |
| 108538 | 3 | 0.25 | 0.48 | 0.57 | 0.25 | 0.38 | 1.10 | 1.39 | 0.36 | 0.39 | 0.49 | 0.00 |
| 108538 | 3 | 0.06 | 0.12 | 0.14 | 0.05 | 0.14 | 0.26 | 0.39 | 0.09 | 0.11 | 0.11 | 0.00 |
| 108538 | 3 | 0.02 | 0.03 | 0.02 | 0.01 | 0.03 | 0.06 | 0.22 | 0.02 | 0.02 | 0.03 | 0.00 |
| 108538 | 3 | 0.00 | 0.00 | 0.00 | 0.00 | 0.01 | 0.02 | 0.08 | 0.00 | 0.00 | 0.01 | 0.00 |
| 108538 | 3 | 0.11 | 0.16 | 0.14 | 0.07 | 0.12 | 0.19 | 1.21 | 0.14 | 0.42 | 0.19 | 0.00 |
| 108538 | 3 | 0.16 | 0.21 | 0.19 | 0.11 | 0.20 | 0.28 | 1.00 | 0.15 | 0.38 | 0.23 | 0.00 |
| 108538 | 3 | 0.00 | 0.00 | 0.00 | 0.00 | 0.00 | 0.00 | 0.00 | 0.00 | 0.00 | 0.00 | 0.00 |
| 108538 | 4 | 0.36 | 0.44 | 0.44 | 0.27 | 0.65 | 0.61 | 1.64 | 0.36 | 0.76 | 0.41 | 0.00 |

| Person | Gmi Meal Smry | Saccharin | Caffeine | Phytic Acid | Oxalic Acid | Methyl | Sucrose Pol | Ash | Water | Pcnt Cal From Fat | Pcnt Cal From Carb | Pcnt Cal From Protein |
|---|---|---|---|---|---|---|---|---|---|---|---|---|
| 108538 | 1 | 0.00 | 0.00 | 230.35 | 2.23 | 0.00 | 0.00 | 1.88 | 200.60 | 14.88 | 69.38 | 16.80 |
| 108538 | 1 | 0.00 | 200.87 | 24.24 | 2.01 | 0.00 | 0.00 | 0.35 | 343.91 | 0.00 | 80.00 | 20.00 |
| 108538 | 1 | 0.00 | 0.00 | 0.00 | 0.13 | 0.00 | 0.00 | 0.73 | 87.40 | 4.64 | 55.57 | 39.07 |
| 108538 | 1 | 0.00 | 0.00 | 12.40 | 113.55 | 0.00 | 0.00 | 2.20 | 197.01 | 3.18 | 99.53 | 17.88 |
| 108538 | 1 | 0.00 | 0.00 | 432.92 | 12.43 | 0.00 | 0.00 | 1.59 | 4.55 | 7.08 | 101.25 | 12.07 |
| 108538 | 1 | 0.00 | 0.00 | 19.37 | 5.04 | 0.00 | 0.00 | 1.01 | 18.29 | 5.24 | 77.67 | 15.27 |
| 108538 | 2 | 0.00 | 0.00 | 0.00 | 68.05 | 0.00 | 0.00 | 0.70 | 65.44 | 4.70 | 101.87 | 4.48 |
| 108538 | 2 | 0.00 | 0.00 | 191.43 | 15.63 | 0.00 | 0.00 | 0.88 | 0.77 | 57.67 | 27.77 | 19.22 |
| 108538 | 2 | 0.00 | 0.00 | 8.01 | 1.33 | 0.00 | 0.00 | 0.36 | 0.84 | 49.87 | 44.47 | 5.49 |
| 108538 | 3 | 0.00 | 0.00 | 223.75 | 142.19 | 0.00 | 0.00 | 2.32 | 66.06 | 3.62 | 74.10 | 24.50 |
| 108538 | 3 | 0.00 | 0.00 | 12.02 | 116.73 | 0.00 | 0.00 | 1.95 | 114.64 | 5.97 | 80.22 | 34.96 |
| 108538 | 3 | 0.00 | 0.00 | 1.96 | 331.58 | 0.00 | 0.00 | 0.55 | 44.81 | 3.68 | 90.55 | 15.27 |
| 108538 | 3 | 0.00 | 0.00 | 0.90 | 8.37 | 0.00 | 0.00 | 0.55 | 8.52 | 3.12 | 104.96 | 5.85 |
| 108538 | 3 | 0.00 | 0.00 | 86.95 | 63.43 | 0.00 | 0.00 | 1.09 | 121.20 | 42.91 | 55.13 | 3.55 |
| 108538 | 3 | 0.00 | 0.00 | 133.66 | 7.39 | 0.00 | 0.00 | 2.10 | 28.08 | 32.89 | 58.85 | 7.91 |
| 108538 | 3 | 0.00 | 0.00 | 2.08 | 4.83 | 0.00 | 0.00 | 0.13 | 71.87 | 0.83 | 102.24 | 1.65 |
| 108538 | 4 | 0.00 | 0.00 | 444.71 | 22.82 | 0.00 | 0.00 | 3.69 | 2.98 | 35.64 | 58.72 | 9.05 |

| Person | Gmi Meal Smry | Pcnt Cal From Alcohol | Pcnt Cal From Sfa | Pcnt Cal From Mufa | Pcnt Cal From Pufa | Poly Fat Ratio | Chol Fat Acid Index | Tran Octadecenoic Acid | Tran Octadecad Acid | Tran Hexadecenoic | Tot Tran Fatty Acids | Tot Sugar |
|---|---|---|---|---|---|---|---|---|---|---|---|---|
| 108538 | 1 | 0.00 | 2.63 | 4.68 | 5.44 | 4.83 | 0.40 | 0.00 | 0.00 | 0.00 | 0.00 | 0.56 |
| 108538 | 1 | 0.00 | 0.00 | 0.00 | 0.00 | 0.00 | 0.00 | 0.00 | 0.00 | 0.00 | 0.00 | 0.00 |
| 108538 | 1 | 0.00 | 3.09 | 1.29 | 0.26 | 0.08 | 0.20 | 0.00 | 0.00 | 0.00 | 0.01 | 4.24 |
| 108538 | 1 | 0.00 | 0.53 | 0.53 | 1.06 | 4.20 | 0.02 | 0.00 | 0.00 | 0.00 | 0.00 | 6.92 |
| 108538 | 1 | 0.00 | 0.68 | 1.18 | 3.84 | 3.10 | 0.13 | 0.00 | 0.00 | 0.00 | 0.00 | 15.85 |
| 108538 | 1 | 0.00 | 0.72 | 0.43 | 2.29 | 1.78 | 0.12 | 0.00 | 0.00 | 0.00 | 0.00 | 0.48 |
| 108538 | 2 | 0.00 | 1.76 | 0.39 | 0.88 | 0.44 | 0.16 | 0.00 | 0.00 | 0.00 | 0.00 | 11.81 |
| 108538 | 2 | 0.00 | 9.08 | 26.44 | 18.70 | 0.58 | 1.49 | 0.09 | 0.02 | 0.00 | 0.10 | 2.59 |
| 108538 | 2 | 0.00 | 12.29 | 28.51 | 6.55 | 0.08 | 1.00 | 1.10 | 0.08 | 0.00 | 1.17 | 0.84 |
| 108538 | 3 | 0.00 | 0.95 | 0.32 | 1.59 | 1.75 | 0.16 | 0.00 | 0.00 | 0.00 | 0.00 | 3.04 |
| 108538 | 3 | 0.00 | 0.70 | 0.35 | 3.16 | 5.60 | 0.02 | 0.00 | 0.00 | 0.00 | 0.00 | 1.83 |
| 108538 | 3 | 0.00 | 0.61 | 0.82 | 1.23 | 1.02 | 0.02 | 0.00 | 0.00 | 0.00 | 0.00 | 4.32 |
| 108538 | 3 | 0.00 | 0.43 | 0.52 | 1.30 | 0.38 | 0.01 | 0.00 | 0.00 | 0.00 | 0.00 | 3.19 |
| 108538 | 3 | 0.00 | 10.71 | 18.74 | 11.27 | 1.85 | 5.06 | 2.60 | 0.74 | 0.00 | 3.34 | 28.53 |
| 108538 | 3 | 0.00 | 14.24 | 12.18 | 3.44 | 0.15 | 4.95 | 0.62 | 0.06 | 0.01 | 0.69 | 10.47 |
| 108538 | 3 | 0.00 | 0.00 | 0.09 | 0.46 | 0.00 | 0.00 | 0.00 | 0.00 | 0.00 | 0.00 | 22.36 |
| 108538 | 4 | 0.00 | 7.41 | 19.06 | 6.47 | 0.76 | 3.19 | 3.39 | 0.27 | 0.00 | 3.65 | 0.43 |

While the invention has been described in connection with what is presently considered to be the most practical and preferred embodiment, it is to be understood that the invention is not to be limited to the disclosed embodiment, but on the contrary, is intended to cover various modifications and equivalent arrangements included within the scope of the appended claims.

The invention claimed is:

1. A computer implemented method for providing nutrient data based on dietary intake that reduces information within a dietary intake data set into combination codes used to index into food portion data, comprising:

reading, into at least one computer system from a dietary food intake source, dietary intake data for dietary intake over a period in excess of a week, said dietary intake data including the United States Department of Agriculture Continuing Survey of Food Intakes by Individuals;

automatically reducing, with said at least one computer system, said United States Department of Agriculture Continuing Survey of Food Intakes by Individuals dietary intake data into a smaller amount of food type code data useful for identifying nutrients in foods actually consumed by dietary intake study participants, said automatically reducing comprising iteratively applying multi-dimensional data reduction coordinates representing food item identification to said dietary intake data to provide combined food type codes, said multidimensional coordinates comprising food form, characteristic, flavor, classification, preparation method, package type and special label codes;

automatically grouping said combined food type codes according to dietary factors relating to nutrient makeup;

mapping, with said at least one computer system, said reduced dietary intake data combined and grouped food type codes with food nutrient information and food portion size information obtained from a source other than said dietary intake source; and generating, with said at least one computer system, an output data set for analysis.

2. A computer implemented method of integrating diet information from multiple data sources to reduce information within a diet intake data set into combination codes used to index into food portion data, comprising:

acquiring, with at least one computer system, dietary intake information on a household level from multiple survey periods, said dietary intake data including the United States Department of Agriculture Continuing Survey of Food Intakes by Individuals;

automatically reducing, with said at least one computer system, said United States Department of Agriculture Continuing Survey of Food Intakes by Individuals dietary intake data into a smaller amount of data useful for identifying nutrients in foods actually consumed by dietary intake study participants, said automatically reducing comprising iteratively applying multi-dimensional data reduction coordinates comprising comprising food form, characteristic, flavor, classification, preparation method, package type and special label codes to provide combined food type codes, and grouping said combined codes according to dietary factors relating to nutrient makeup;

assigning each member of a household an individual ID; and correlating, with said at least one computer system, said dietary intake information to said assigned individual IDs.

3. A computer implemented method of providing dietary intake analysis that reduces information within a dietary intake data set into combination codes used to index into food portion data, comprising:

acquiring, with at least one computer system, a dietary intake data set, said dietary intake data including the United States Department of Agriculture Continuing Survey of Food Intakes by Individuals;

selecting, with said at least one computer system, data fields within said data set that describe food items;

automatically reducing, with said at least one computer system, said selected fields to a food code by iteratively applying multi-dimensional data reduction coordinates comprising food form, characteristic, flavor, classification, preparation method, package type and special label codes to provide combined food type codes, and grouping said combined codes according to dietary factors relating to nutrient makeup; and using said food code to provide linkage to further data structures specifying portion size and/or nutrient value.

4. A computer implemented method of extracting individual dietary intake information from a dietary intake data set that reduces information within a dietary intake data set into combination codes used to index into food portion data, comprising:

maintaining a household master file with at least one computer system;

reading, with said at least one computer system, food intake information associated with at least one individual from said dietary intake data set, said dietary intake data including the United States Department of Agriculture Continuing Survey of Food Intakes by Individuals;

automatically reducing, with said at least one computer system, said dietary intake data by iteratively applying multi-dimensional data reduction coordinates comprising food form, characteristic, flavor, classification, preparation method, package type and special label codes to provide combined codes, and grouping said combined codes according to dietary factors relating to nutrient makeup;

testing, with said at least one computer system, whether said read food intake information corresponds to an individual previously specified within said household master file; and conditionally assigning and writing, with said at least one computer system into said household master file, based at least in part on said testing step, an identifier corresponding to said individual, said assigned identifier being different, from any identifier used by said data set in association with said individual.

5. The method of claim 4 wherein said dietary intake data set spans multiple dietary intake survey reporting time periods, said testing step recognizes the same individual surveyed in said multiple dietary intake survey time periods, and said assigning and writing step is conditioned to not assign and write a different identifier for the same individual reporting in different survey reporting time periods.

6. A computer implemented method of providing nutrient intake information that reduces information within a dietary intake data set into combination codes used to index into food portion data, comprising:

reading, with at least one computer system, dietary intake information from a dietary intake data set including food description information, said dietary intake data including the United States Department of Agriculture Continuing Survey of Food Intakes by Individuals;

automatically reducing, with said at least one computer system, said food description information to a code, said reducing including iteratively applying a multi-dimensional data reduction coordinates comprising food type codes including food form, characteristic, flavor, classification, preparation method, package type and special label codes to provide combined codes, and groups said combined codes according to dietary factors that relate to nutrient makeup;

using said at least one computer system to look up said code within a data structure;

generating, with said at least one computer system, an exception if said code is not predefined within said data structure; and if said code is predefined within said data structure, said at least one computer system using said data structure to associate nutrient and/or portion size information with said code.

7. A computer implemented method of generating a food descriptor code that reduces information within a dietary intake data set into combination codes used to index into food portion data, comprising:

reading, with at least one computer system, plural food descriptor fields from a dietary intake data set, said dietary intake data including the United States Department of Agriculture Continuing Survey of Food Intakes by Individuals;

iteratively looking up, with said at least one computer system, said food descriptor field values to generate plural corresponding combination codes;

concatenating, with said at least one computer system, said plural combination codes together into a food descriptor code including by iteratively applying multi-dimensional data reduction coordinates to comprising food form, characteristic, flavor, classification, preparation method, package type and special label codes to provide combined food type codes, and groups said combined codes according to dietary factors that relate to nutrient makeup; and said at least one computer system using said food descriptor code to link with further data.

8. The method of claim 7 wherein said further data comprises a recipe.

9. The method of claim 7 wherein said further data comprises a nutrient data set.

10. The method of claim 7 wherein said further data comprises a portion size data set.

11. The method of claim 7 wherein said further data comprises demographics data.

12. A computer system for extracting individual dietary intake data information from a dietary intake data set that reduces information within a dietary intake data set into combination codes used to index into food portion data, comprising:
 a storage medium storing a household master file;
 a reader that reads food intake information associated with at least one individual from said dietary intake data set, said dietary intake data including the United States Department of Agriculture Continuing Survey of Food Intakes by Individuals;
 a data reducer including means for reducing the amount of data within said dietary intake data by iteratively multi-dimensional data reduction coordinates comprising food form, characteristic, flavor, classification, preparation method, package type and special label codes to provide combined food type codes and groups said combined codes according to dietary factors that relate to nutrient makeup;
 a tester that tests whether said food intake information corresponds to an individual previously specified within said household master file; and
 an identifier assigned that conditionally assigns and writes into said household master file, based on the testing results of said tester, an identifier corresponding to said individual, said assigned identifier being different from any identifier used by said data set in association with said individual.

13. The system of claim 12 wherein said dietary intake data set spans multiple dietary intake survey reporting time periods, said tester recognizes the same individual surveyed in said multiple dietary intake survey time periods, and said identifier assigner is conditioned to not assign and write a different identifier for the same individual reporting in different survey reporting time periods.

14. A data processing system for providing nutrient intake information that reduces information within a dietary intake data set into combination codes used to index into food portion data, comprising:
 a mass storage device that stores a dietary intake data set including food description information, said dietary intake data including the United States Department of Agriculture Continuing Survey of Food Intakes by Individuals;
 a reduction computer including means for reducing said food description information to a code, by iteratively applying a multi-dimensional data reduction coordinates comprising food form, characteristic, flavor, classification, preparation method, package type and special label codes to provide combined food type codes, and grouping said combined codes according to dietary factors that relate to nutrient makeup;
 a data structure that stores certain codes; and
 a tester coupled to said data structure and to said reduction computer, said tester including means for generating an exception if said code is not predefined within said data structure and using said data structure to associate nutrient and/or portion size information with said code if said code is predefined within said data structure.

15. A computer system for generating a food descriptor code that reduces information within a dietary intake data set into combination codes used to index into food portion data, comprising:
 a dietary intake data set including plural food descriptor fields, said dietary intake data including the United States Department of Agriculture Continuing Survey of Food Intakes by Individuals;
 a table;
 a data reducer including means for reducing said dietary intake data by iteratively applying multi-dimensional data reduction coordinates comprising food form, characteristic, flavor, classification, preparation method, package type and special label codes to provide combined food type codes and groups said combined codes according to dietary factors that relate to nutrient makeup, said data reducer including:
  an iterative referencer means for iterative looking up said food descriptor field values within said table to generate plural corresponding combination codes; and
  a concatenator means for concatenating said plural combination codes together into a food descriptor code.

16. The system of claim 15 wherein said further data comprises a recipe.

17. The system of claim 15 wherein said further data comprises a nutrient data set.

18. The system of claim 15 wherein said further data comprises a portion size data set.

19. The system of claim 15 wherein said further data comprises demographics data.

20. A data processing system for analyzing nutrient intake data that reduces information within a dietary intake data set into combination codes used to index into food portion data, comprising:
 a mass storage device that stores a large dietary intake data set including food description information and having rows and columns, said dietary intake data including the United States Department of Agriculture Continuing Survey of Food Intakes by Individuals;
 a data reducer coupled to said mass storage device, said data reducer including means for reducing said dietary intake data set into a smaller amount of data for use in identifying the nutrients in foods consumed by dietary intake study participants, said data reducer means combining codes for various food types by iteratively applying an eight-dimensional data reduction coordinates comprising food form, characteristic, flavor, classification, preparation method, package type and special label codes, within the dietary intake data set and for grouping said codes according to dietary factors that relate to the nutrient makeup of the foods, said grouping means operating based on a lookup table including at least the following keys:
  a combination key representing a unique sequential value identifying a portion of a unique character code,
  a category code identifying a general food group type,
  a column number pointing to a column in the food intake data set, and
  a column value designating one or more values that apply to a given column/category,
 a data mapper means for mapping said reduced dietary intake data with at least a nutrient value data set and food portion size information; and
 an output generator that generates mapped output results.

21. The system of claim 20 wherein said data reducer means scans a data reduction table to determine whether a particular food within the dietary intake data set has been defined within he lookup table and has a corresponding combination key.

22. The system of claim 20 wherein said data reducer means performs multiple iterative scans to yield additional combination keys that may be combined together to provide a combination code for particular food items identified in the food intake data set.

23. The system of claim 20 wherein said data reducer means creates a combination code food descriptor corresponding to a food-portion link data file storing information about foods that have been previously defined by combining a portion size data set with a nutrition data set for a particular food descriptor code.

24. The system of claim 20 wherein said data reducer means maps reduced unique food designators to food descriptor combination codes found within a food portion link file.

25. The system of claim 20 wherein said data reducer means generates exceptions when new food items are determined to exist within said dietary intake data set so a dietary intake scientist can dynamically update the lookup table to include new food items.

26. A method of reducing dietary intake data including the following steps performed at least in part by a data processing system that reduces information within a dietary intake data set into combination codes used to index into food portion data:

maintaining a combination key file;

selecting a subset of fields comprising type, form, character, flavor, classification, preparation method, package type, and special label, from the fields defined by a large food intake data set, said dietary intake data including the United States Department of Agriculture Continuing Survey of Food Intakes by Individuals, looking up each column name and column value corresponding to said selected fields in the combination key file;

forming a character key based on the record number of items found within the combination key file;

looking up the formed character key in a food-portion link file;

determining whether said character code exists within a nutrient value data set;

outputting the character code with additional identifying information if said character code does not exist within the nutrient value data set to request a nutrient value analysis; and respectively performing the above-mentioned steps until said food intake data set has been processed.

* * * * *